United States Patent [19]

Niehaus et al.

[11] Patent Number: 5,147,185
[45] Date of Patent: Sep. 15, 1992

[54] PUMP APPARATUS FOR FLUID SAMPLING AND COLLECTION, AND THE LIKE

[75] Inventors: K. Lynn Niehaus, Manchester; Kevin L. Newcomer, Monroe; Steven C. Richter, Ann Arbor, all of Mich.

[73] Assignee: QED Environmental Systems, Inc., Ann Arbor, Mich.

[21] Appl. No.: 660,333

[22] Filed: Feb. 22, 1991

Related U.S. Application Data

[63] Continuation-in-part of Ser. No. 522,629, May 14, 1990.

[51] Int. Cl.$^5$ .................................... F04B 47/08
[52] U.S. Cl. .................................. 417/394; 417/478
[58] Field of Search .......................... 417/478, 394

[56] References Cited
U.S. PATENT DOCUMENTS

| | | | |
|---|---|---|---|
| 3,007,416 | 11/1961 | Childs | 417/394 X |
| 3,148,624 | 9/1964 | Baldwin | 417/478 |
| 4,990,745 | 2/1991 | Bayles | 392/384 |

FOREIGN PATENT DOCUMENTS

| | | | |
|---|---|---|---|
| 195758 | 9/1986 | European Pat. Off. | 417/394 |
| 257781 | 10/1989 | Japan | 417/397 |

Primary Examiner—Leonard E. Smith
Attorney, Agent, or Firm—Harness, Dickey & Pierce

[57] ABSTRACT

A liquid pump apparatus is disclosed for pumping groundwater samples, contaminants or other fluids from a well, monitoring site, tank, vessel, or the like. The pump apparatus is applicable in systems including dedicated wellhead assemblies permanently installed at such wells or monitoring sites in order to minimize cross-contamination from site to site. Another application of the pump apparatus for recovery, collection and control system for cleanup of leachate or other liquid material or contaminated groundwater from a landsite is also disclosed. The pump apparatus according to the invention includes check valve means adapted to accommodate vertical, horizontal, non-vertical, or even inverted pump orientations, without requiring a high level of static head in order to function properly.

2 Claims, 15 Drawing Sheets

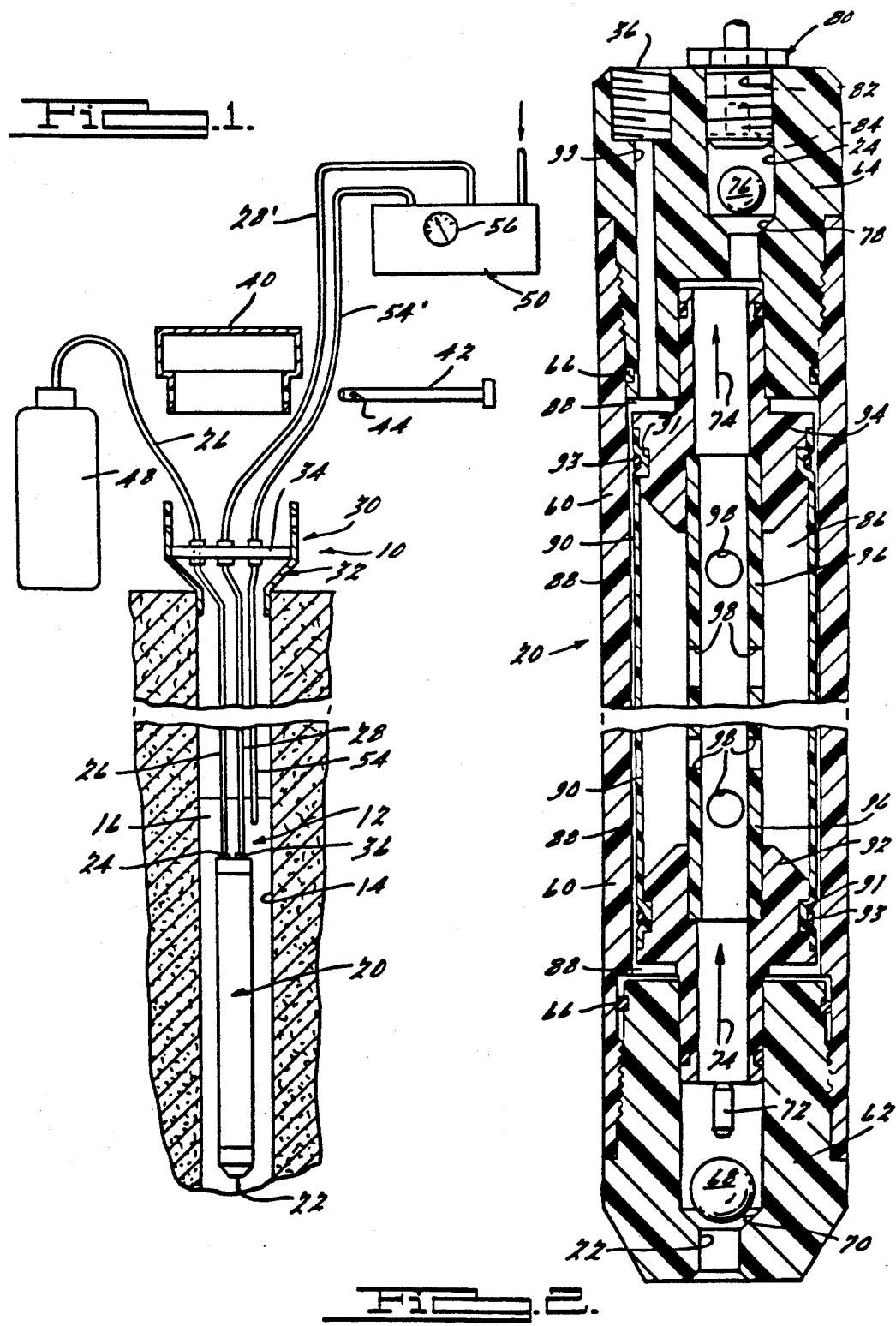

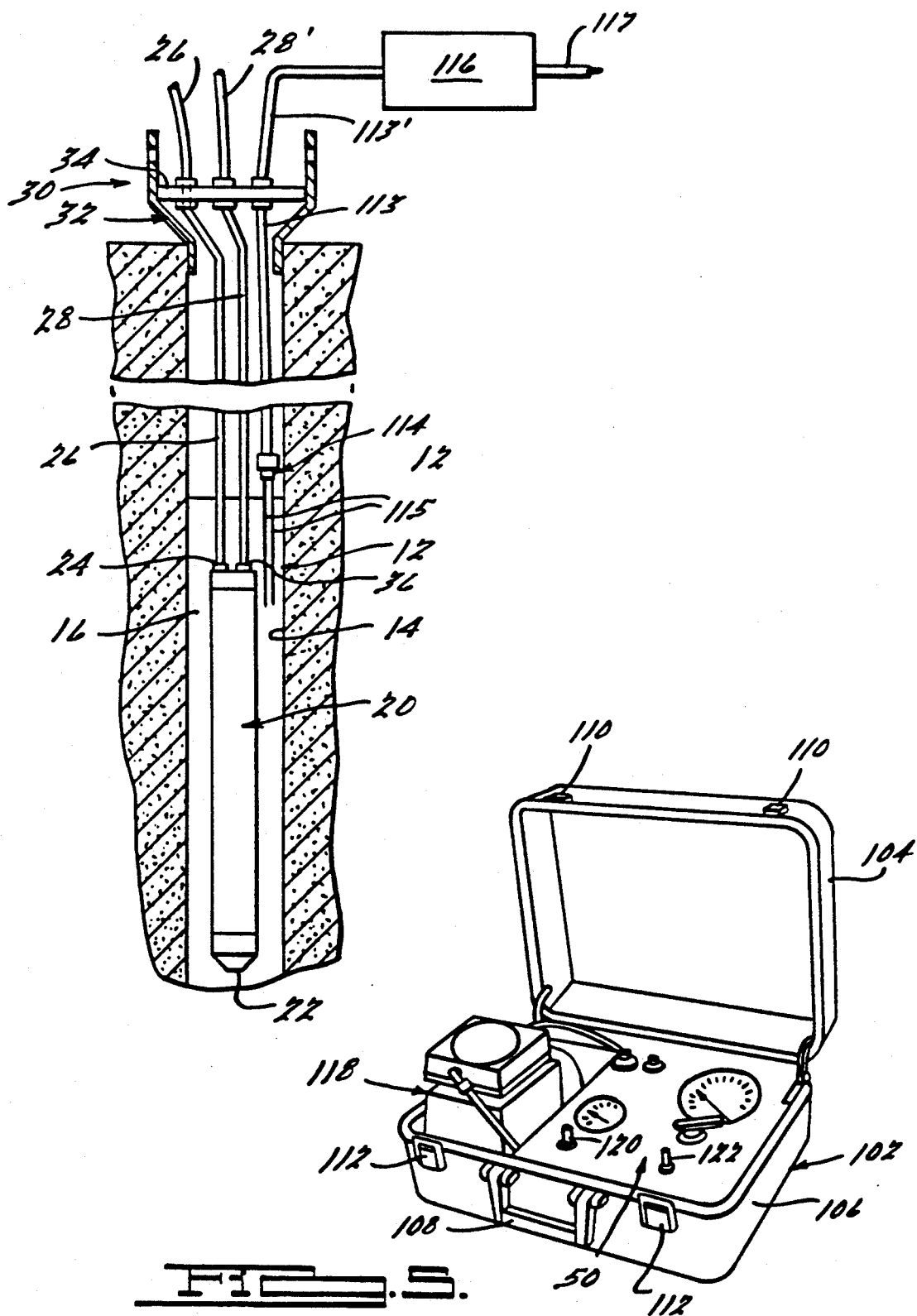

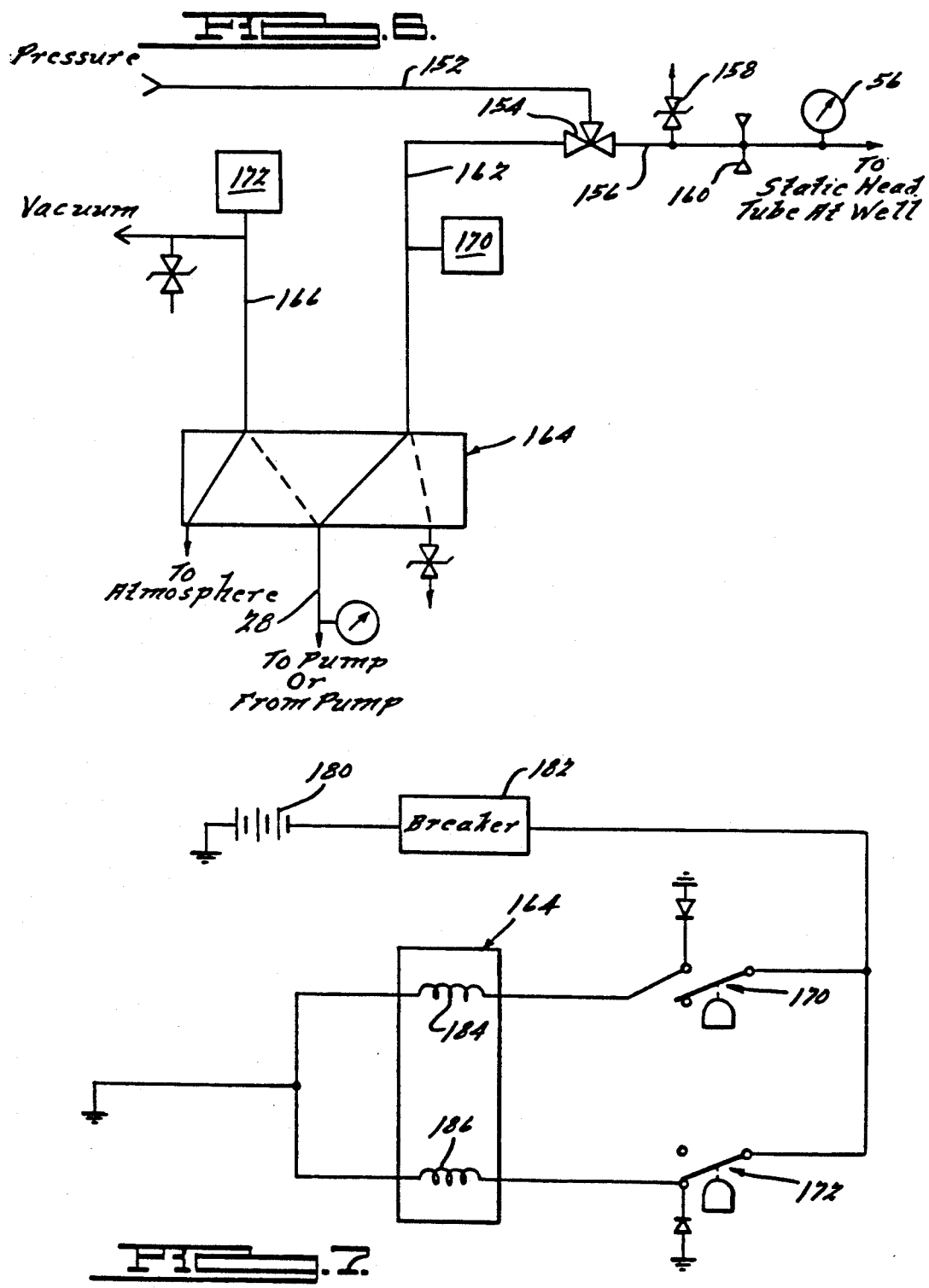

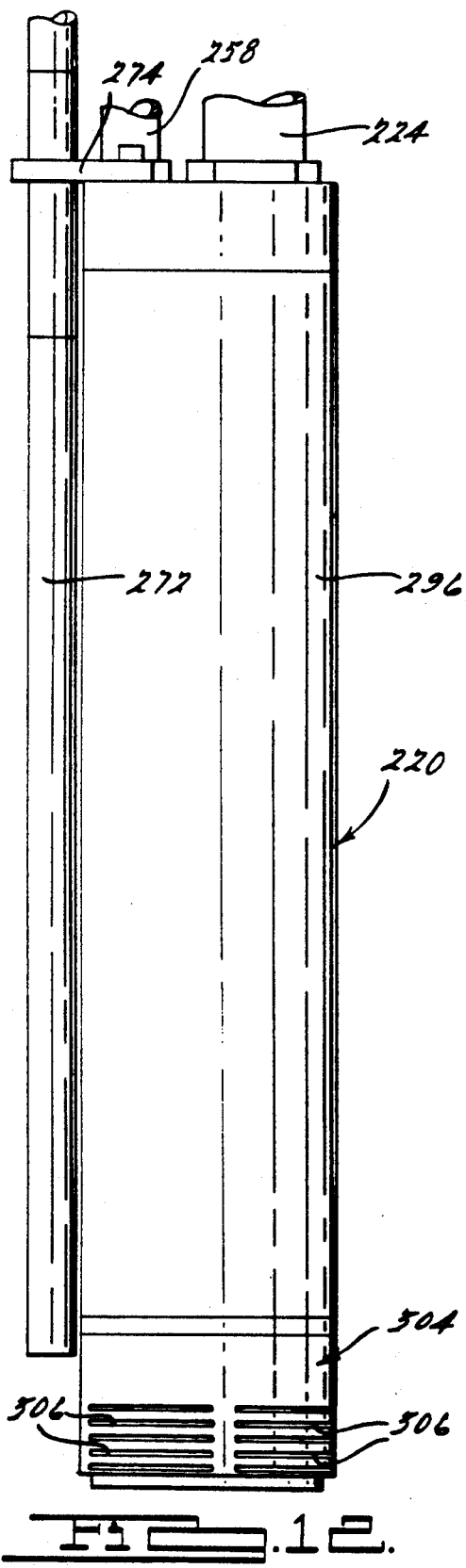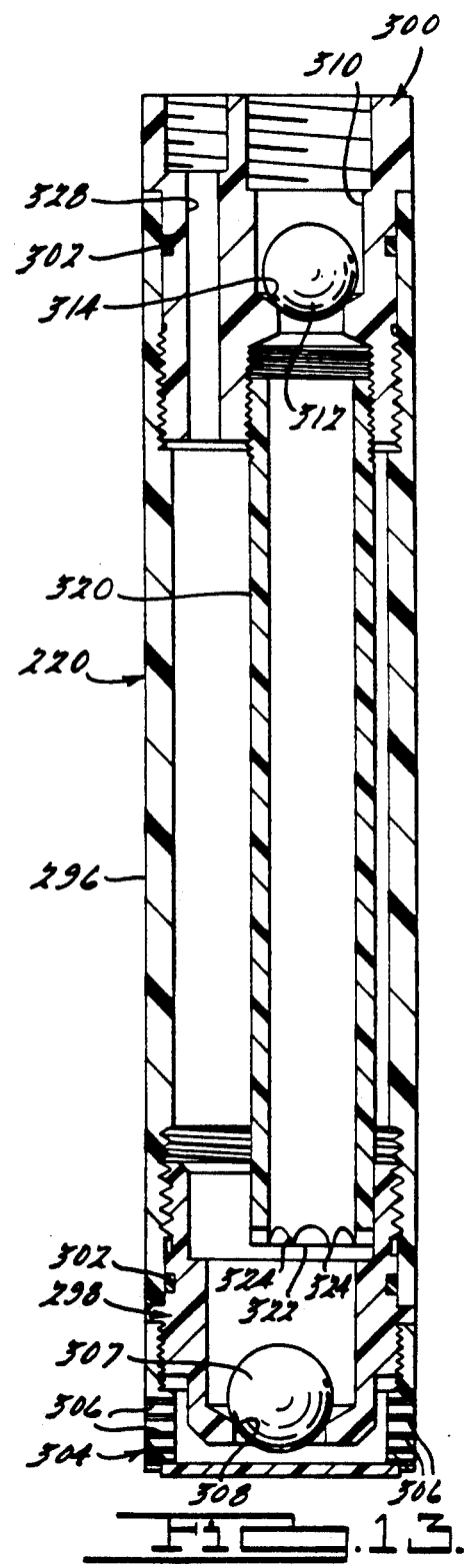

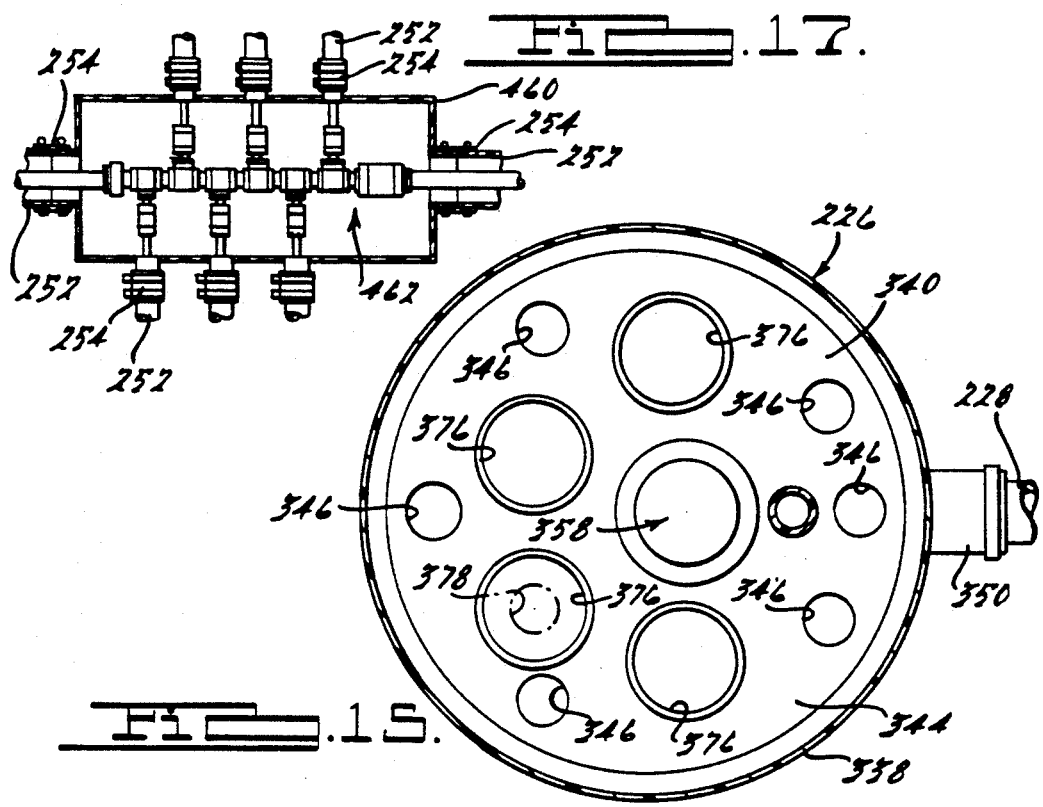
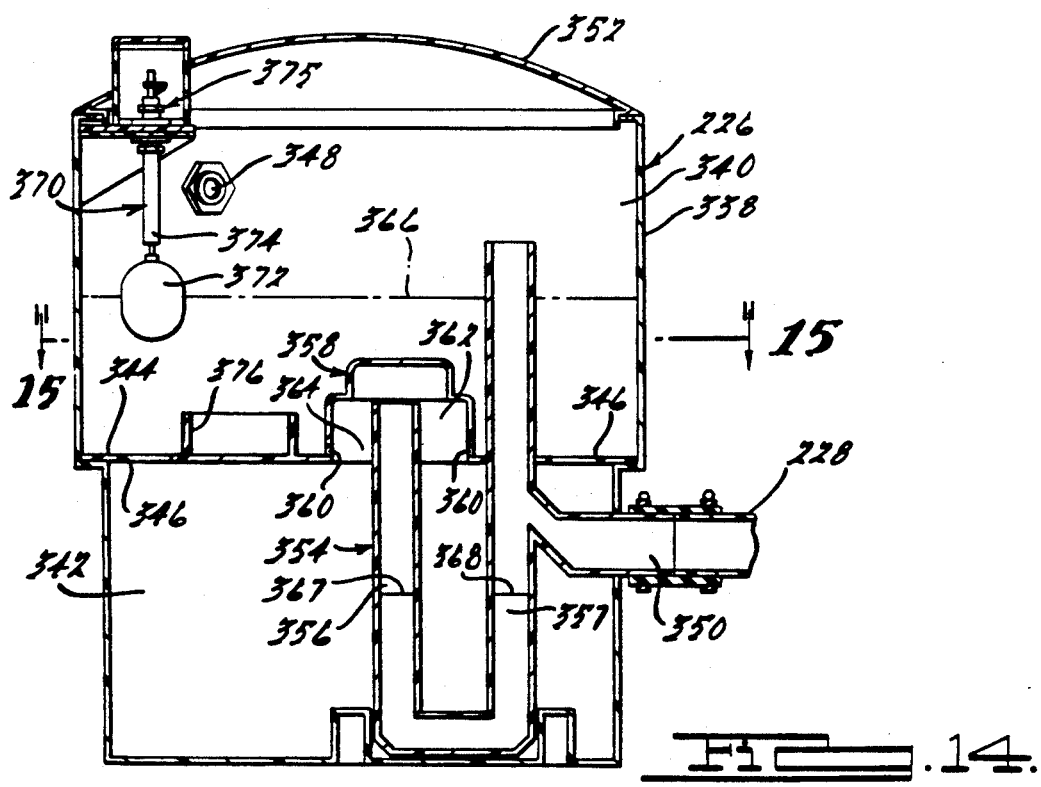

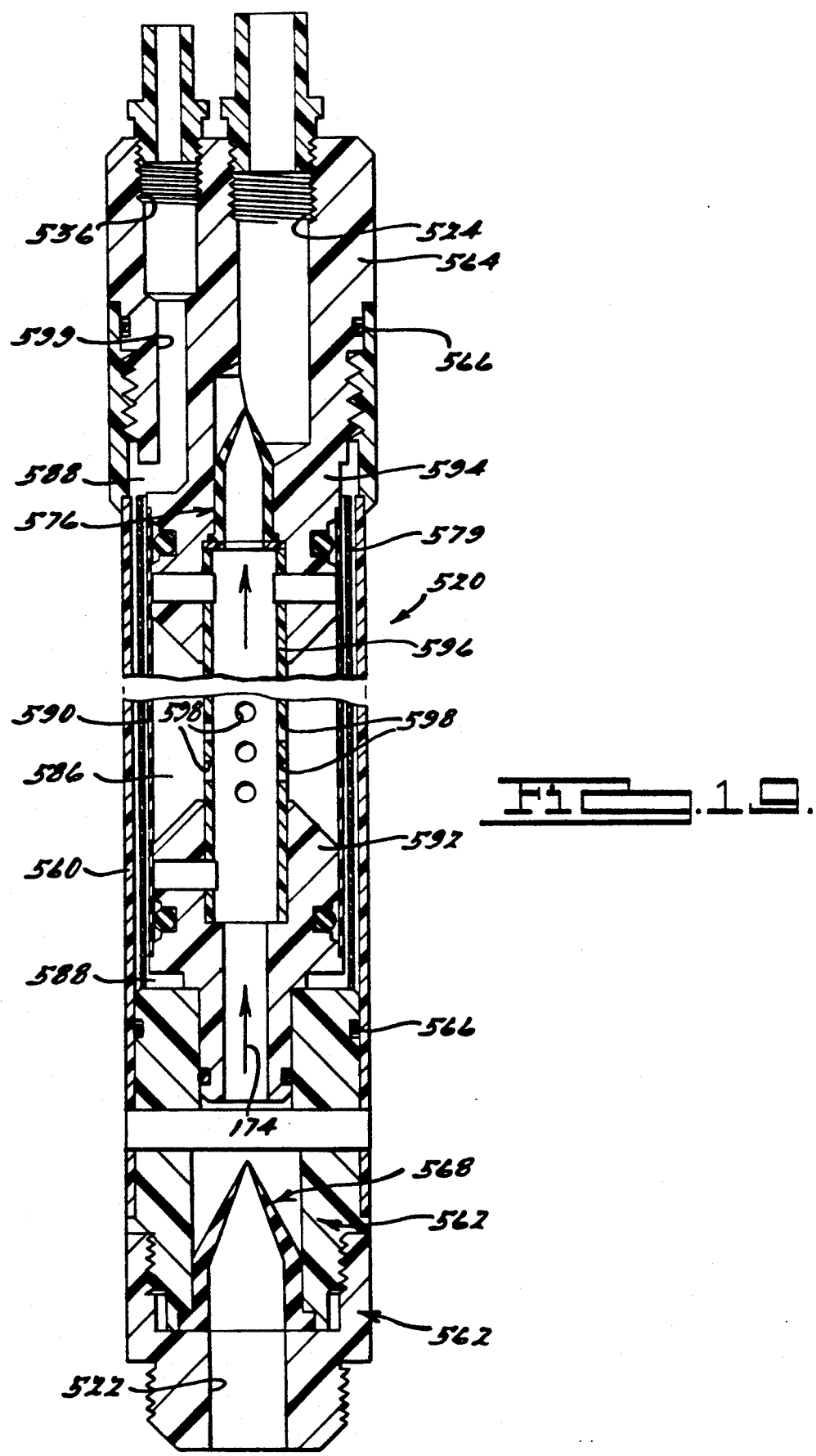

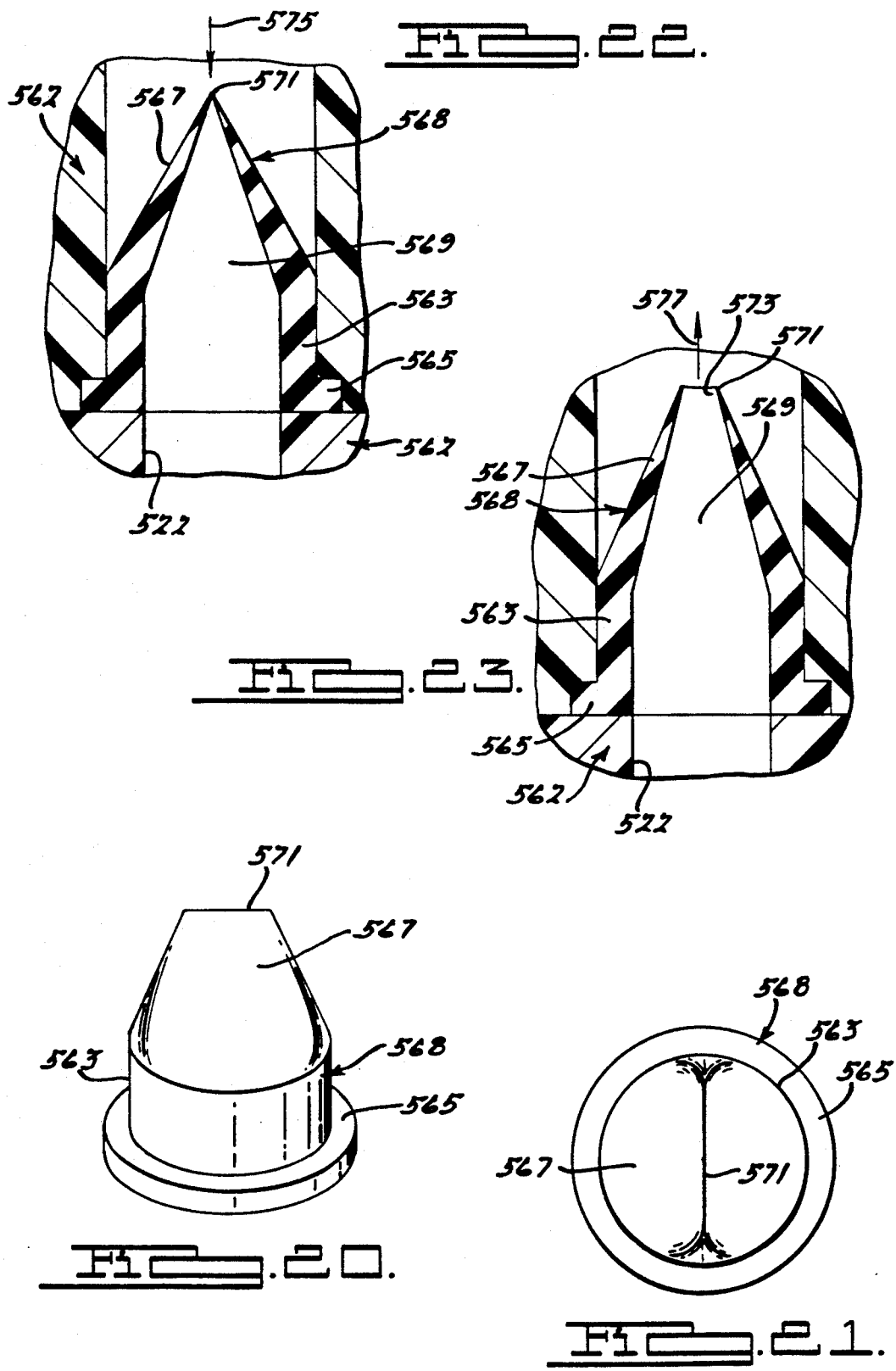

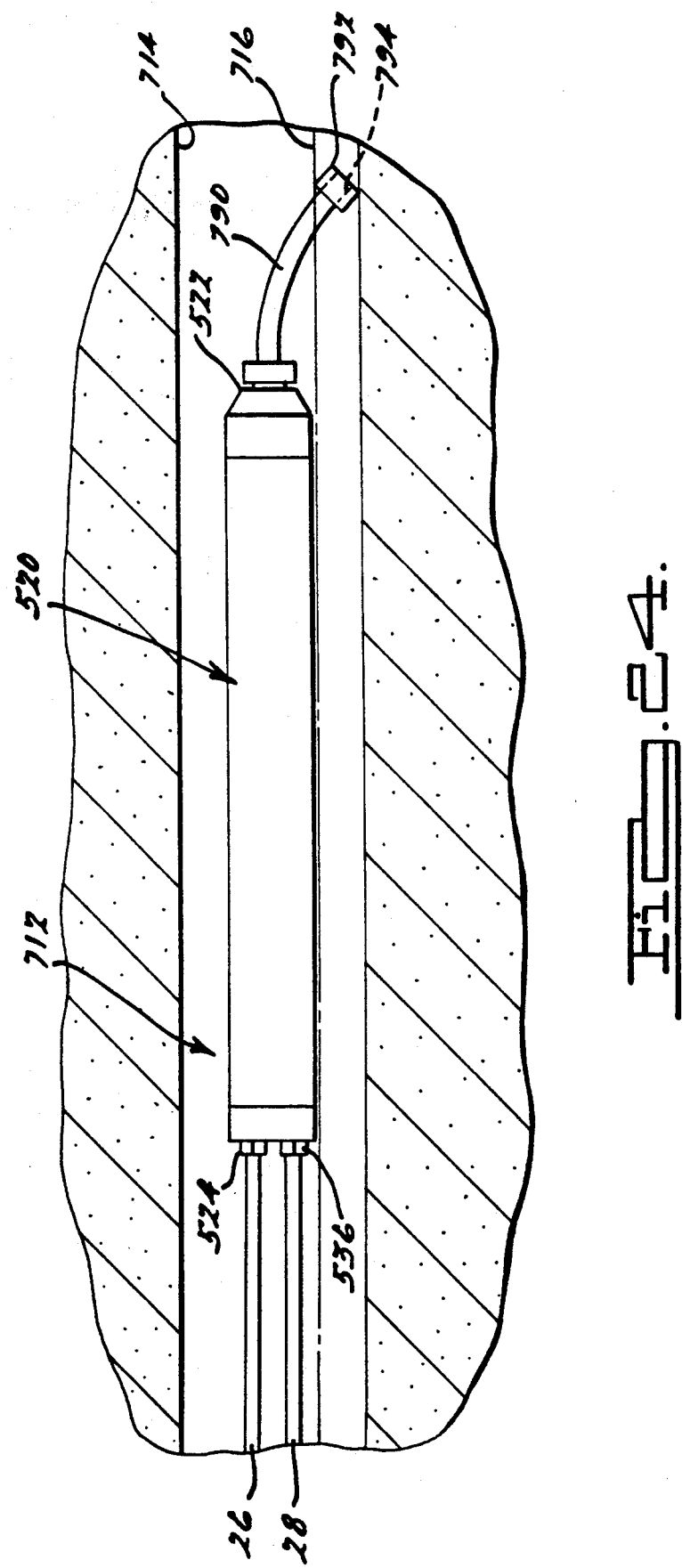

PUMP APPARATUS FOR FLUID SAMPLING AND COLLECTION, AND THE LIKE

This application is a continuation-in-part of U.S. application Ser. No. 07/522,629, filed May 14, 1990 which is a continuation of U.S. application Ser. No. 07/436,546, filed Nov. 14, 1989, now U.S. Pat. No. 4,998,585. This application is also related to U.S. Pat. Nos. 4,489,779; 4,585,060; and 4,727,936.

BACKGROUND AND SUMMARY OF THE INVENTION

The invention relates generally to fluid pumping and collection apparatuses. More particularly, the present invention relates primarily to such apparatus for pumping, recovering, collecting, or controlling fluids such as groundwater samples, condensate, hazardous leachate materials, or contaminated fluids from sources such as contaminated landsites having one or more in-ground wells, for example, or to or from tanks or other vessels. It should be noted, however, that the invention is also applicable and adaptable in various other applications that will occur to one skilled in the art from the disclosure herein, and that the invention allows for pumping in substantially any pump orientation.

Recent increases in public concern for the environment have resulted in various government-imposed environmental regulations with regard to groundwater quality and landsite cleanup projects. Among such regulations are requirements relating to the monitoring and sampling of groundwater quality. In response to these requirements, water quality analytic capabilities have ben improved and water sampling equipment has been developed. Much of the previously-developed sampling equipment has not been effective, however, in obtaining consistent, non-contaminated water samples that are accurately representative of the water system from which the sample is taken. Such ineffectiveness is especially acute in situations where vertical pump orientations are impossible or impractical.

The inadequacies of previous sampling equipment stem largely from causes such as cross-contamination between sampling sites, ineffective and inconsistent field cleaning methods, contamination due to equipment handling, and inconsistent well depth sampling. In addition to present sample quality problems, much of the previous equipment has been heavy and bulky and thus difficult to transport from one monitoring site to another. Finally, much of such previous equipment has proved to be complicated to operate, inordinately expensive, impractical for sampling at remote locations where site access is severely limited, and/or unusable in applications that require pump orientations other than substantially vertical.

The cleanup of toxic or otherwise hazardous materials from contaminated dump sites has also presented monumental environmental problems, especially in terms of safety, effectiveness, and economics. Many of the hazardous materials present in such contaminated landsites, or other fluid materials in other applications, are difficult and dangerous to handle, convey, and collect, especially in situations where the fluid is practically inaccessible to pumping equipment that requires a vertical orientation, as well as often being highly aggressive and corrosive to many materials commonly used for removal and collections equipment construction. In addition, many hazardous materials give off, or are accompanied by, explosive gases, making the use of conventional electrically-operated equipment at contaminated landsites dangerous and undesirable. Finally, because of the potentially dangerous nature of many of the hazardous materials at such landsites, human intervention in the operation and maintenance of cleanup systems and equipment must be minimized.

In response to the groundwater monitoring and hazardous waste cleanup problems discussed above, the above-mentioned issued patents and co-pending applications relate to fluid sampling apparatuses provided for use in obtaining accurate samples of groundwater or other fluids. In one preferred embodiment of the disclosed groundwater sampling equipment, for example, a groundwater sampling pump is dedicated to a particular monitoring well or other sampling site in order to substantially avoid cross-contamination of samples for site-to-site and is constructed from lightweight, non-contaminating materials.

One of the preferred pumps for sampling or other pumping applications is a submersible, fluid-actuated pump wherein the actuating fluid is preferably a gas such as air. A flexible bladder member in this type of pump separates and isolates the interior of the pump into two chambers; a first chamber that contains the sample fluid and is in communication with both the pump inlet and outlet, and a second chamber surrounding the first chamber, and connected to a source of the actuating gas, with the bladder disposed therebetween. The pumped fluid is conveyed through the pump by alternately pressurizing and venting or relieving the pressure in the second chamber to contract and relax the bladder member, thus alternately decreasing and increasing the volume of the first chamber. The pumped fluid is drawn into the first chamber during such increases in volume under the influence of the natural hydrostatic head of the groundwater or other pumped fluid and is discharged through the pump outlet during such decreases in volume, thereby conveying the pumped fluid through the pump. The components of this pump are preferably composed of low-cost, lightweight synthetic materials that are non-corrosive and do not otherwise affect the chemical composition of the sampled fluid, but other materials, such as stainless still can alternately be used in appropriate liquid pumping applications. In this regard, it should be stressed that the present invention is not limited to such bladder-type pumps and is equally applicable to other types of pumps.

In order to allow the pump to be used in non-vertical orientations, that is in orientations greater than approximately 30 degrees from vertical, the preferred pump (whether a bladder-type or a non-bladder pump) includes rather unique reed-type check valves that render the pump functional in such non-vertical orientations, in substantially horizontal orientations, or even in inverted orientations. Such reed check valves are primarily used in gas conveying applications, but have been found to be highly advantageous in liquid pumping applications, according to the present invention, due to the fact that such reed check valves require only very low pressure levels to operate. In contrast, conventional check valves capable of functioning in non-vertical orientations, such as those employing a ball-and-seat arrangement with a spring return, require much higher pressures in order to function.

Also, in applications requiring substantially horizontal pump applications, the pump can include a flexible hose-like fluid conduit attached at one end in fluid communication with the pump inlet, with the other, open hose inlet end being submerged in the liquid to be pumped. In this embodiment, the open hose inlet end can be weighted in order to deflect the flexible hose downwardly, thus facilitating pumping down to minimum liquid levels in such horizontal, or near-horizontal, orientations.

When used for sampling, for example, the pump can be preferably dedicated to, and thus remains in, a particular sampling site or well, which is substantially isolated from the above-ground surroundings by a wellhead assembly in order to reduce potential contamination during sampling. A portable controller apparatus can be provided with quick connect-disconnect means and means for alternately pressurizing and de-pressurizing the actuating fluid. The fluid sampling apparatus, or other such apparatus, may also optionally include means for measuring the standing level, and thus the hydrostatic had, of the fluid in the well, tank, vessel, or other liquid source.

Besides relating generally to the above-described groundwater quality applications, another of the primary objects of the present invention is to provide a pump usable in the recovery, collection, and control system for the removal of hazardous leachate or other liquid materials, wherein the system and equipment are relatively simple and economical to install, operate, and maintain, and require a minimum of human intervention. The present invention also seeks to provide such a pump applicable to systems wherein the recovery, collection, and control system and equipment do not require the presence of electricity and are composed of materials that are resistant to, and substantially unaffected by, the corrosive and destructive nature of many hazardous materials. In addition, the present invention is, of course, directed to improving the safety, effectiveness, and wide applicability of such equipment.

According to the present invention, a pump is provided for a wide variety of applications, including but not limited to withdrawing and collecting a flowable hazardous leachate material, a contaminated groundwater, or other subterranean liquids from a landsite having a plurality of in-ground wells, and especially in systems where in accessibility or other factors substantially preventing a vertical, upright pump orientation, thus requiring a horizontal, non-vertical, or even inverted orientations. The system can include a plurality of pumps, each of which is adapted for installation in one of the in-ground wells at the landsite, can have an associated fluid control apparatus for supplying and controlling an operating fluid to the pump, and can be installed in small-diameter wells, generally in the range of approximately two inches to approximately ten inches in diameter, for example. As mentioned above, the present invention renders a pump especially advantageous for pumping from horizontally, or near-horizontally, drilled wells below waste sites for sampling or cleanup.

The system can also involve collection equipment for receiving and collecting the leachate or other liquid material withdrawn by the fluid-operated pumps. Such collecting equipment can also include one or more flow totalization devices for receiving and collecting the leachate material from the pumps, with piping or other conveying apparatus being provided for conveying the leachate or other liquid material from the pumps to the totalization device and for conveying the collected leachate or other material from the flow totalization device to holding or disposal equipment.

Such a flow totalization device according to one exemplary application of the present invention includes a cyclable discharge device that is self-actuable and self-deactuable for discharging the collected leachate or other material to the holding or disposal equipment during each actuation/deactuation cycle of operation. In such an arrangement, a counter device is preferably providing for counting the number of actuation/deactuation cycles, in which a predetermined volume of liquid material is charged during each cycle. The counter device thus allows the total volume of collected liquid material discharged from the flow totalization device to be measured and accounted for over a preselected time period. In systems employing a number of such flow totalization devices, each receiving liquid material from a number of the plurality of pumps, the invention preferably includes a common disposal or holding tank into which the flow totalization devices are discharged. Alternately, the flow totalization devices may be discharged directly into a railway tank car, a tank truck, or other portable collection receptable, which when full can be replaced and transported away for appropriate disposal or treatment of the hazardous material.

The preferred leachate recovery pumps for withdrawing the leachate material from the in-ground wells are air-operated, gas-displacement pumps, each having a generally hollow cylindrical body submersible in the in-ground well. The pump body includes a water, leachate, or other liquid inlet with an inlet reed check valve such as that described above for allowing substantially one-way fluid flow from the in-ground well into the housing interior, and a water, leachate, or other liquid outlet with a similar outlet reed check valve allowing substantially one-way fluid flow from the pump body interior to the discharge conveying and collection equipment. A discharge tube is disposed within the pump body and has an inlet end that is open to the pump body interior. It should again be noted that in this preferred form of pump according to the present invention, the inlet and outlet check valves are capable of allowing the pump to function in any orientation, including vertical and upright, generally horizontal, non-vertical, or even inverted orientations, whether or not a bladder-type pump or other type of pump is used.

An exemplary control apparatus in some applications for supplying and controlling an operating fluid for a gas-displacement pump pulsatingly supplies a pressurized operating fluid, such as air, into the pump body interior in order to forcibly displace and discharge leachate or other liquid material through the discharge tube and the outlet. Between pressurized pulses of the operating fluid, the control apparatus relieves the pressure of the other operating fluid in the pump body interior in order to permit liquid material to flow, under the influence of its own hydrostatic head, into the pump housing through The inlet. The preferred control apparatus in such exemplary applications is all pneumatic and also includes conveniently-adjustable level sensing device for sensing the level of the leachate or other liquid material in the in-ground well in order to selectively actuate and deactuate the pump in response to respective high and low liquid levels in the in-ground well. In addition, a second level sensing system can also be provided for sensing the level of collected material in a central holding or collection apparatus and is interconnected with the control apparatus to deactuate the recovery pump (or pumps) when the collection or holding apparatus is too full to accept more liquid material. The control apparatus then prevents further actuation of the pumps until the central collection apparatus is emptied, replaced, or otherwise rendered capable of receiving additional collected liquid material.

Additional objects, advantages and features of the present invention will become apparent from the following description and appended claims taken in conjunction with the accompanying drawings.

BRIEF DESCRIPTION OF THE DRAWINGS

FIG. 1 is a partially-exploded, longitudinal sectional view of a fluid sampling system.

FIG. 2 is a longitudinal cross-sectional view of the fluid sampling pump of FIG. 1.

FIG. 4 is a schematic representation of an optional apparatus for measuring the static head of the groundwater of the monitoring well of FIG. 1.

FIG. 6 is a schematic representation of the fluid-actuating system of an alternate controller apparatus.

FIG. 7 is a schematic representation of the electrical system of the alternate controller apparatus of FIG. 6.

FIG. 8 is a diagrammatic plan view of a contaminated landsite including a recovery, collection, and control system according to the present invention, for withdrawing and collecting leachate or other flowable liquid material from a plurality of in-ground wells.

FIG. 12 is an elevational view of the recovery pump shown in FIG. 9.

FIG. 13 is a longitudinal cross-sectional view of the recovery pump of FIG. 12.

FIG. 14 is a cross-sectional view of a flow totalization unit of the system illustrated diagrammatically in FIG. 8.

FIG. 15 is a view taken generally along line 15—15 of FIG. 14.

FIG. 17 is a representative illustration, partially in cross-section, of a preferred piping junction apparatus for the various piping systems employed in a recovery, collection and control system.

FIG. 19 is a longitudinal cross-sectional view similar to that of FIG. 2, but illustrating the improved pump of FIG. 1 according to the present invention.

FIG. 20 is a perspective view of an exemplary reed check valve member of the pump of FIGS. 18 through 19.

FIG. 21 is a top view of the reed check valve member of FIG. 20.

FIG. 22 is a longitudinal cross-sectional view of the red check valve member of FIGS. 20 and 21, shown in its closed position.

FIG. 23 is a longitudinal view similar to that of FIG. 22, but showing the reed check valve member in its open position.

FIG. 24 is a view similar to that of FIG. 18A, but illustration another pump having a flexible inlet hose with a weighted hose inlet end.

DETAILED DESCRIPTION OF THE PREFERRED EMBODIMENTS

Figure 3:
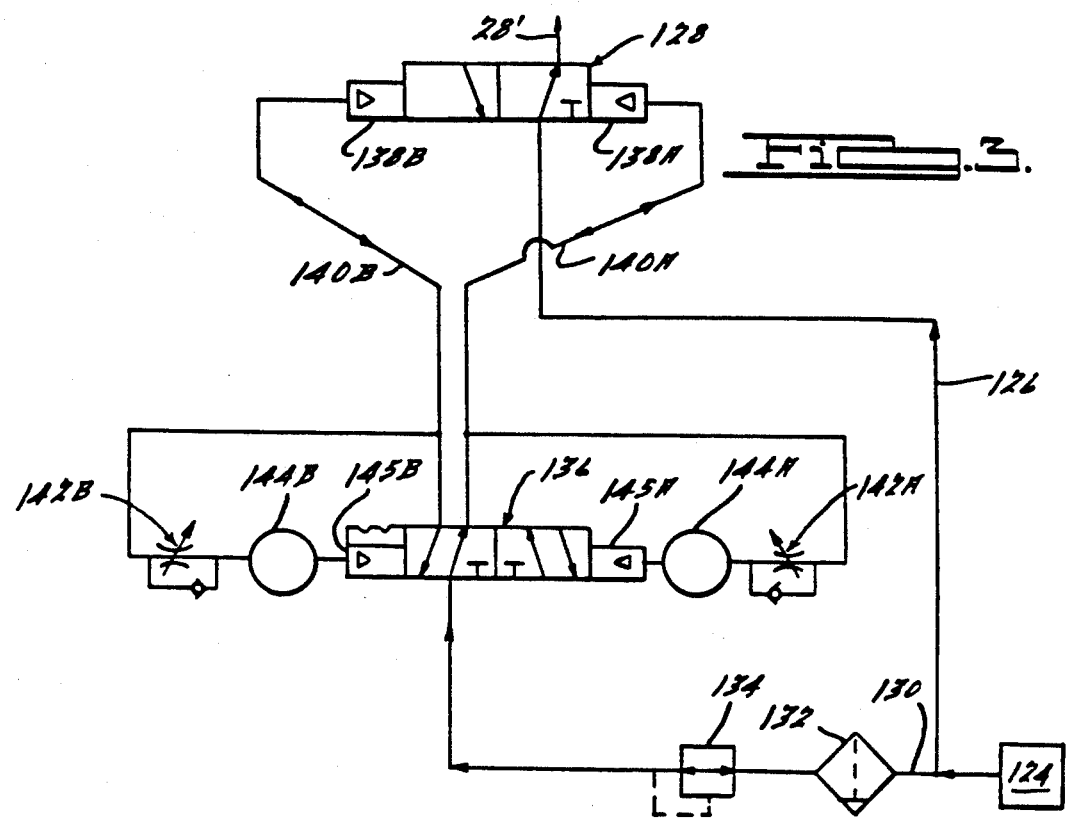
FIG. 3 is a schematic representation of the preferred controller apparatus of FIG. 1.

For purposes of background and illustration, FIGS. 1 through 24 of the drawings depict exemplary application of an inventive pump for fluid conveying apparatus installed in monitoring wells for withdrawing samples of groundwater or other fluids therefrom, for example. One skilled in the art will readily recognize from the following discussion and the accompanying drawings and claims that the principles of the invention are equally applicable to fluid conveying apparatuses other than that shown in the drawings as well as to other fluid pumping apparatuses.

FIGS. 8 through 17 depict an exemplary system, in which a pump according to the present invention can be advantageously applicable, for withdrawing, collecting, and controlling flowable hazardous leachate material, at a landsite having a plurality of in-ground wells. As will be readily apparent to one skilled in the art from the following discussion and the accompanying drawings and claims, a pump apparatus according to the present invention is not limited to leachate recovery and collection systems, or to the exemplary embodiments of other such systems depicted in the drawings. Rather, the present invention is equally applicable in various other fluid flow systems or operations. Some examples of the various other applications of the present invention include the following, among many others: recovery of groundwater samples or contaminated groundwater from landsites; landfill gas well dewatering; pumping of hazardous or flammable liquids from tanks, containers, or ponds; groundwater gradient control, miscible or immiscible produce recovery; gas production well dewatering; cleanup of liquid spills, especially for flammable or other hazardous liquids; secondary containment or leak detection; or in other similar applications as will occur to one skilled in the art from the disclosure herein.

In this regard it should be noted that FIGS. 1 through 17 are shown in order to provide background for the present invention and/or exemplary, illustrative applications of the present invention, while exemplary embodiments of the present invention are illustrated primarily in FIGS. 18 through 24. In this regard, although bladder-type, gas-actuated pumps are shown for purposes of illustration only, the present is equally applicable to other types of pumps.

In FIG. 1, an exemplary fluid sampling apparatus is indicated generally by reference numeral 10 and is shown for purposes of illustration as installed in a monitoring well 12, which preferably includes a well riser or casing 14. A fluid sampling pump 20 is disposed within the well casing 14 of the monitoring well 12 and is submerged beneath the level o the groundwater 16 to a suitable depth for obtaining accurate and representative groundwater samples.

As is explained in further detail below, one preferred fluid sampling pump 20 is a fluid-actuated pump, wherein the actuating fluid is preferably a gas such as air, for example, and includes an inlet port 22 and an outlet port 24. A wellhead assembly 30 is secured to the well casing 14 and includes a wellhead body portion 32 having a generally horizontal support plate 34 therein. The wellhead body portion 32 substantially isolates the interior of the well 12 from the above-ground surrounding environment in order to avoid, or at least minimize, contamination of the interior of the well which would result from contact between the groundwater 16 and the air or other elements. The wellhead assembly 30 also includes a groundwater conduit 26 sealingly connected at one end to the pump inlet 22 and passing through plate 34 to provide direct sample delivery to a sample collection vessel 48. A gas conduit 28 is connected at one end to a gas connection 36 on the pump 20 and at the other end to the support plate 34. Because the pump is preferably of a lightweight construction, the conduits themselves can frequently be used to hold and retain the pump in its submerged position in the well.

A controller apparatus 50, which is described in further detail below, is selectively and removably connected to the wellhead assembly 30 by means of external gas conduit 28'. The preferred controller apparatus 50 is a potable, lightweight unit and includes a source of an actuating gas and means for alternately positively pressurizing and venting or relieving the pressure of the actuating gas in order to operate the fluid sampling pump 20, as is explained below.

In order to further isolate the interior of the well 12 from above-ground contamination, the wellhead assembly 30 preferably includes a closure member 40 adapted to be secured to the body portion 32 by a locking pin 42 insertable through corresponding aligned apertures in the body portion 32 and in the closure member 40. The locking pin 42 preferably includes an aperture 44 at one end, through which a padlock or other suitable locking means can be inserted in order to substantially prevent unauthorized access to the interior portions of the wellhead assembly.

The wellhead assembly 30 can also optionally include a static head or measuring liquid conduit 54 having an open end extending beneath the surface of the groundwater 16 and an opposite end connected to the support plate 34. The controller apparatus 50 is connectable to the static head conduit 54 by means of an external static head or measuring fluid conduit 54' and includes means for supplying a measuring fluid to the static conduit 54. Such measuring fluid, which can be air, for example, is supplied at a pressure sufficient to force the groundwater out of the open end of the static head conduit 54. The pressure necessary to expel the groundwater from the open end of the static head conduit can be measured by a pressure measuring device, schematically represented by reference numeral 56, in order to determine the standing level of groundwater in the well 12. The standing level of the groundwater 16 is determined for purposes such as detecting changes in quantities of subterranean groundwater or for determining the volume of groundwater in the monitoring well so that the well may be purged of approximately three to five times the standing volume of groundwater in the well before the sample is taken.

Referring to FIG. 2, the fluid sampling pump 20 includes a generally hollow cylindrical pump body 60 having an inlet cap 62 and an outlet cap 64 preferably threadably attached to its opposite ends. The inlet and outlet caps 62 and 64, respectively, are sealed to the pump body 60 by means of O-rings 66 or other suitable sealing means known to those skilled in the art. The inlet cap 62 includes the inlet port 22 and check valve means for preventing backflow of groundwater or other fluids through the inlet port 22 from the interior of the pump. Such check valve means in pumps prior to the present invention includes a ball 68 trapped between a ball seat 70 and a retainer member 72. The retainer member 72 can be a relatively thin and flat insert frictionally held in place within the enlarged portion of the inlet pot 22. Thus, when groundwater is flowing properly through the pump in the direction indicated by flow arrows 74, the groundwater may flow around the ball 68 and the retainer member 72 into the interior of the pump. Backflow in a direction opposite that indicated by flow arrows 74 is substantially prevented by sealing engagement of the ball 68 with its ball seat 70. Similarly, the outlet cap 64 includes check valve means comprising ball 76 trapped between ball seat 78 and outlet fitting 80. Thus, flow through the pump in the direction indicated by flow arrows 74 is allowed to pass around the ball 76 and through the slot 84 and bore 82 of the outlet fitting 80. Backflow is substantially prevented, however, by sealing engagement of the ball 76 with its ball seat 78.

The interior of the pump body 60 is divided and isolated into two chambers by a generally cylindrical flexible bladder 90. The bladder 90 defines a groundwater chamber 86 in its interior and defines an annular gas chamber 88 between the bladder exterior and the interior wall surface of the pump body 60. The bladder 90 is sealingly connected to the spool pieces 92 and 94 at its opposite ends by means of rings 93 which are swaged or otherwise deformed to sealingly force the bladder material into the grooves 91 on the spool pieces 92 and 94. The rings 93 may be composed of a soft ductile metal or other readily deformable material known to those skilled in the art. A connecting tube 96 in the groundwater chamber 86 extends between the spool pieces 92 and 94 and includes a number of apertures 98 spaced at various locations along its longitudinal length in order to allow the free flow of groundwater fluid between the interior of the connecting tube and the remainder of the groundwater chamber 86.

Referring to FIGS. 1 and 2, one preferred fluid sampling pump 20 is actuated by means of an actuating gas supplied to the gas chamber 88 which is alternately and sequentially subjected to positive and negative or reduced pressures. The alternate pressurizing and depressurizing of the actuating gas in the gas chamber 88 causes the bladder 90 to alternately contract and relax, thus alternately and sequentially decreasing and increasing the volume of the groundwater chamber 86. During such increases in volume, groundwater is drawn from the well 12 into the groundwater chamber 86 through the inlet port 22 in the inlet cap 62. During such decreases in such volume, the groundwater is forced out of the groundwater chamber 86 through the outlet port 24 in the outlet cap 64 and is passed through the groundwater conduit 26 to be collected in the sample collection vessel 48. The check valve means in each of the inlet and outlet caps 62 and 64, respectively, prevent the water from being discharged through the inlet port or drawing in through the outlet port. The capacity of the pump 20 may be changed in different versions of the pump by increasing the length of the pump body 60, and correspondingly increasing the length of the bladder 90 and the connecting tube 96, thereby changing the amount of water drawn in and forced out during the alternate contractions and relaxations of the flexible bladder 90.

It should be noted that except for the swaged rings 93, which do not contact the groundwater, the various components of the pump 20 are preferably composed of relatively lightweight and low-cost synthetic materials (or stainless steel, or other suitable metallic alloys) that will not be corroded when exposed to the groundwater 16 and that will not otherwise affect the composition of the groundwater flowing through the pump. Examples of such materials include rigid polyvinyl chloride (PVC) or virgin grade tetrafluoroethylene (TFE) teflon. The flexible bladder is preferably composed of a flexible synthetic material which also will not corrode or affect the composition of groundwater flowing therethrough, such as flexible polyvinyl chloride, TFE, or VITON, for example. VITON is a trademark owned by E.I. Du Pont de Nemours & Company for its fluoroelastomer materials. One skilled in the art will readily recognize, however, that the various components of the fluid sampling apparatus may be composed of other suitable non-corrosive materials.

The preferred controller apparatus 50 generally includes the external gas conduit 28' and means for supplying an actuating or operating gas to the gas chamber 88 of the pump 20 and for sequentially and alternately pressurizing and venting or depressurizing the actuating gas, as described above, in order to actuate the fluid sampling pump. The various individual components of the preferred controller apparatus 50 are well-known to those skilled in the art and thus are described in FIGS. 3 and 3A only schematically in terms of their functions.

As is represented schematically in FIG. 3, a pressurized actuating gas, such as air, for example, is supplied from an actuating gas source 124, such as a gas compressor, pressurized gas containers, or even a hand-operated pump, for example, through a gas supply line 126. The pressurization and vent cycles for the sampling pump are controlled by the action of three-way supply valve 128, which is in fluid communication with the gas source through the supply line 126. In its first valving mode, which is shown in FIG. 3, the three-way supply valve 128 connects the compressed gas source 124 to the gas conduit 28' and the sampling pump in order to contract the flexible bladder 90 and expel groundwater from the pump. In its second valving mode, supply valve 128 vents the gas conduit 28' to the open atmosphere thereby allowing groundwater to flow into the pump under the influence of its natural hydrostatic head. The supply valve 124 automatically alternates the pressurization and venting conditions by means of a pneumatic timing circuit.

Pressurized actuating gas from the gas source 124 is also conveyed through a conduit 130 to a filtration coalescence device 132 and then to a pressure regulator 134, which maintains gas pressure levels appropriate to proper functioning of the timing circuit components. The pressure-regulated gas flow is fed continuously to the control shuttle valve 136, which is a five-way type valve and which directs the pressure-regulated gas to one of the two pilot actuators 138A an 138B of the three-way supply valve 128 and to the corresponding pilot actuator 145A and 145B of the control shuttle valve 136.

When the control shuttle valve 136 is in its first valving mode shown in FIG. 3, the pilot actuator 138A on the supply valve 128 is pressure-actuated through a conduit 140A, and the pilot actuator 138B is vented to atmosphere. When conduit 140A is pressurized, gas also flows at a controlled rate through an adjustable orifice in a flow control valve 142A and into a gas volume chamber 144A. When the gas pressure in the gas volume chamber 144A exceeds a predetermined level, the control shuttle valve 136 is driven by its pilot actuators 145A and 145B into its second valving mode. In such second mode, the gas in the gas volume chamber 144A and conduit 140A are bled through the adjustable orifice and a reversed check valve in the flow control valve 142A to be vented to atmosphere through the shuttle valve 136. Simultaneously while the control shuttle valve is in such second mode, the previously vented conduit 140B is now pressurized, causing the pilot actuator 138B of the three-way valve 128 to be actuated. The pressure in conduit 140B also causes gas to flow through an adjustable orifice in flow control valve 142B and into a gas volume chamber 144B. When the gas pressure in the gas volume chamber 144B exceeds predetermined level, control shuttle valve 136 is actuated to again pressurize conduit 140A and to again vent conduit 140B to atmosphere. The gas volume chamber 144B is then vented to atmosphere through the flow control valve 142B. The pressurization of conduit 140A this again begins the actuation of the pilot actuator 138A on the supply valve 128 and the resultant pressurization of gas volume chamber 144A to repeat the cycle.

The adjustment of the orifices in the flow control valves 142A and 142B control the rate at which the gas pressure rises in the gas volume chambers 144A and 144B. Thus, the conduits 140A and 140B are alternately pressurized and vented to atmosphere for time periods that are controlled by the as flow rates through flow control valves 142A and 142B and by the size of gas volume chambers 144A and 144B. The gas pressure cycles in conduits 140A and 140B in turn actuate the pilot actuators 138A and 138B of the three-way supply valve 128, thus alternately pressurizing and venting the as conduit 28 and the sampling pump.

Figure 3A:
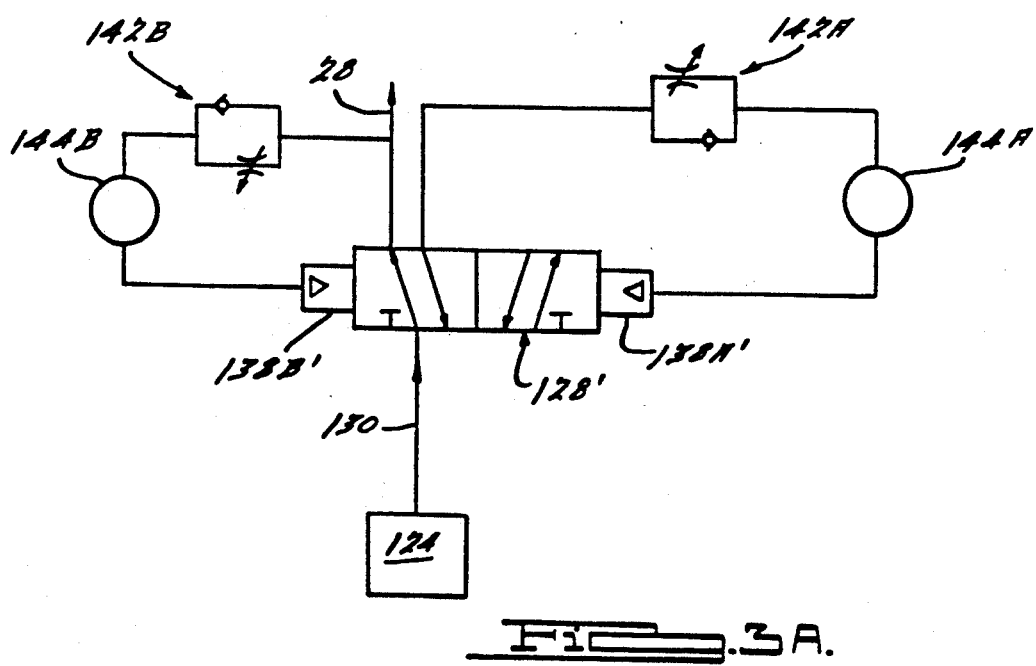
FIG. 3A is a schematic representation of an alternate variation on the controller apparatus of FIG. 3.

Alternate means may also be provided for automatically-cycling the three-way supply valve 128 between pressurization and venting cycles. For example, electronic times may control an alternate solenoid-operated version of the valve 128, with one time controlling the duration of each position or valving mode of the supply valve 128. An alternate pneumatic control circuit may also be provided for the supply valve, as represented schematically in FIG. 3A, with direct control of five-way valve 128' being accomplished by the pneumatic timing elements 142A, 144A, 142A and 144B described above, but without an intermediate control shuttle valve, such as the valve 136 of FIG. 3, and without the pressure regulator 134 or filter 132. One skilled in the art of pneumatic control devices would readily recognize that the selection between the systems of FIGS. 3 and 3A is based upon considerations of reliability, of operation, economy, and flexibility, given the particular application contemplated for the present invention.

FIG. 4 schematically illustrates an electronic version of the optional apparatus for measuring the hydrostatic head of the groundwater 16 in the monitoring well 12. It should be noted that such electronic version of the static head measuring apparatus may alternatively and optionally be employed in conjunction with either of the embodiments of the controller apparatus 50 shown in FIGS. 3 and 3A, or in conjunction with the controller apparatus schematically shown in FIGS. 6 and 7 and discussed below.

The optional static head measuring system schematically represented in FIG. 4 includes an electrical line 113 attached to the support plate 34 of the wellhead assembly 30 and extending into the monitoring well 12. The electrical line 113 is connected to a fluid level sensor 114, which preferably includes a pair of spaced apart electrical probe elements 115 extending into the groundwater 16. The probe elements 115, which are located closing adjacent one another relative to the distance from the probes to the casing 14 of the well, measure electrical quantities, such as conductivity or resistance, across the gap between the probe elements. Since the groundwater and the air above the groundwater have distinct electrical conductivities and resistances, the electrical signal generated by the fluid level sensor changes as the level of the air-water interface correspondingly rises or falls along the probe elements 115. Such electrical signal therefore changes in accordance with any changes in the standing water level in the monitoring well.

The electrical line 113 is connectable, by way of a quick connect-disconnect fitting at the support plate 34, to an external electrical line 113' leading to an electronic processor 116. The processor 116, which preferably comprises a conventional microprocessor unit or other electronic circuitry known in the art, is adapted to receive and differentiate between the varying signals for the fluid level sensor 114 as the level of the air-water interface changes. The processor 116 is also adapted to generate an output signal, through an electrical output line 117 to indicating devices, such as gauges, indicator lights, or the like, on the controller apparatus in order to detect and quantify such changes in the groundwater level in the well.

It should also be noted that alternatively only a single probe element 115 is necessary to measure the level of the groundwater in the well if another electrode is located on the pump body or some other location in the general vicinity of the fluid level sensor 114 and is electrically connected to the processor 116. In such a case the single probe would measure conductivity or resistance between itself and such an electrode and would generate a signal corresponding to the level of the groundwater.

Figure 5:
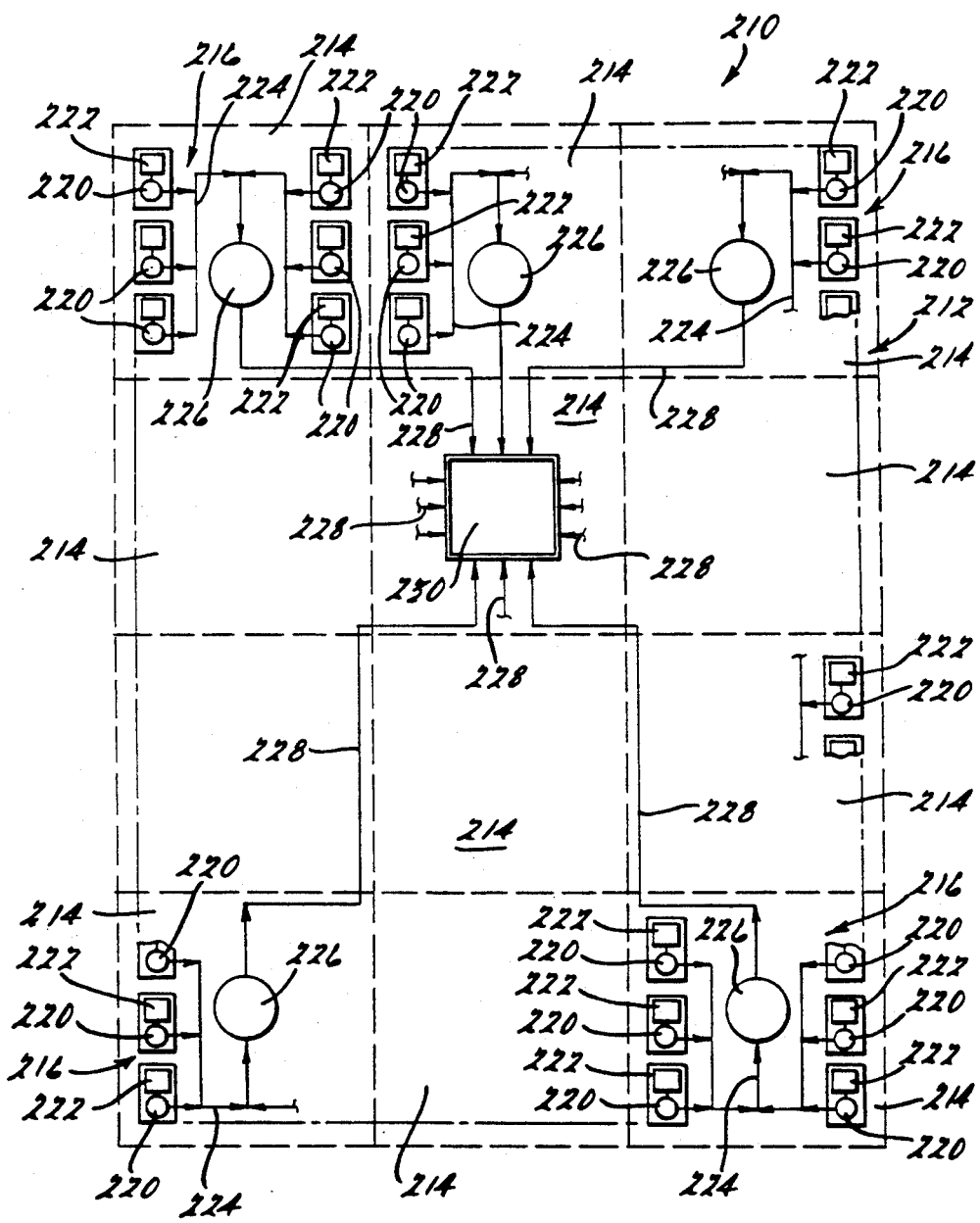
FIG. 5 is an overall perspective view of the controller apparatus of FIG. 1, shown housed in a portable carrying case.

FIG. 5 illustrates a preferred physical arrangement for the controller apparatus 50, including a carrying case 102 for housing and transporting the portable controller apparatus from one monitoring site to another. The carrying case 102 generally includes an upper portion 104 hingedly connected to a base portion 106, carrying handle means 108, and upper and lower latching means 110 and 112. The carrying case 102 is preferably composed of high impact-resistant materials known to those skilled in the art for purposes of protecting the components of the controller apparatus. In the preferred embodiment shown for purposes of illustration in FIG. 5, the controller apparatus generally includes a gas compressor 118, a fitting 120 to which the external gas conduit 28' may be connected, a fitting 122 to which the external static head conduit 54' may be connected (or an electrical connector for the electronic head measuring system of FIG. 4), a power source for the gas compressor 118, and various controls and fluid gauges. The carrying case 102 is especially adapted for ease and convenience of transportation of the controller apparatus and related components to monitoring sites to which access is limited or difficult.

FIG. 6 schematically represents an alternate actuating gas system for an alternate controller apparatus 50. The various physical components of such alternate system are well-known to those skilled in the art and therefore will be described herein only schematically in terms of their functions. A positively or negatively pressurized actuating gas, such as air, for example, is supplied from an actuating gas source, such as a gas compressor, pressurized gas containers, or even a hand-operated pump, for example, through a gas supply line 152. If optional pneumatic apparatus for measuring the standing level of groundwater in the well 12 is to be included in the fluid sampling apparatus 10, the actuating gas may be supplied through the as supply line 152 to a three-way valve 154. During groundwater standing level measurement, the three-way valve 154 is adjusted to divert the actuating gas through a conduit 156 for use as a measuring fluid to determine the standing groundwater level. The conduit 156 includes a safety valve 158, a pressure reducer 160 having a fixed or adjustable restrictive orifice and the pressure measuring device 56 referred to above, which preferably comprises a pressure gauge readable in inches of water. The actuating gas, which also functions as the measuring fluid, is conveyed through the static head conduits 54' and 54 at a pressure sufficient to force substantially all of the groundwater 16 out of the open end of the static head conduit 54. The pressure of the actuating gas/measuring fluid stabilizes as the groundwater is expelled from the open end of the static head conduit, and a static head pressure reading may then be taken on the pressure measuring device 56. The pressure measuring device 56 is previously calibrated so that its readings (in inches of water) may be compared with a previously-measured standing water level in the well 12 when the fluid sampling apparatus 10 was installed therein. Such stabilized pressure reading may thus be compared with the previous calibration level, thereby allowing determination of the standing groundwater level during subsequent measurements. It should be pointed out that the optional and alternate version of the static head measuring apparatus discussed herein in connection with the alternate controller apparatus of FIGS. 6 and 7 may also optionally and alternatively be employed in conjunction with the controller apparatus embodiments of FIGS. 3 and 3A, discussed above.

In order to pump a quantity of the groundwater 16 from the well 12, the three-way valve 154 is adjusted to divert the actuating gas from the gas supply line 152 to a shuttle valve 164 through a connecting line 162. A similar connecting line 166 interconnects the supply valve 164 with a vacuum or negative pressure source. The pressure connecting line 162 and the vacuum connecting line 166 include a pressure switch 170 and a vacuum switch 172, respectively, for actuating the shuttle valve 164 as described below.

When the supply valve 164 is in the valving mode or position illustrated by solid lines in FIG. 6, positively pressurized actuating gas is admitted to the gas chamber of the fluid sampling pup through the gas conduits 28' and 28 as shown in FIG. 1. Such positively pressurized actuating gas causes the pump bladder to contract in order to expel groundwater from the pump as described above. When the pressure switch 170 senses a predetermined positive pressure value in the pressure connecting line 162, it automatically cases the supply valve to switch to the valving mode or position indicated by broken lines in FIG. 6 in order to connect the gas chamber of the fluid sampling pump to the vacuum connecting line 166. The gas chamber of the fluid sampling pump is then subjected to a negative pressure in order to cause the flexible bladder to expand or relax to draw groundwater into the pump through the inlet port 22. Such expansion or relaxation continues until the vacuum switch 172 senses a negative pressure in the vacuum connecting line 166 of a predetermined negative pressure value. At such time the vacuum switch 172 causes the supply valve 164 to revert back to its valving mode shown in solid lines in FIG. 6, thereby reconnecting the gas chamber of the fluid sampling pump to the source of pressurized actuating gas by way of the pressure connecting line 162. Thus, as is described above, the gas chamber of the fluid sampling pump is alternately and sequentially subjected to positive and negative actuating gas pressures thereby causing the flexible bladder to alternately contract an relax in order to cause the groundwater 16 to flow through the pump. Such alternate pressurizing and depressurizing of the gas chamber of the fluid sampling pump continues until the above-discussed purging of the well and withdrawal of a groundwater sample is complete.

FIG. 7 schematically represents an electronic schematic of a control system for use in conjunction with the actuating gas system shown schematically in FIG. 6. Preferably, a portable power source 180 and a circuit breaker 182 are connected to parallel switching circuits, one of such circuits including the pressure switch 170 and its associated electric actuator device 184 and the other of such circuits including the vacuum switch 172 and its associated electric actuator device 186. Thus, when the vacuum switch 172 senses a negative gas actuating fluid pressure equal to the above-mentioned predetermined value, the switch is closed to energize the electric actuator device 186 which causes the supply valve 164 to connect the fluid sampling pump to the pressurized actuating gas source as discussed above in connection with FIG. 6. Alternatively, when the pressure switch 170 senses an actuating gas pressure at the above-mentioned predetermined positive pressure value, the pressure switch closes to energize the electric actuator device 184 which causes the supply valve 164 to disconnect the source of pressurized actuating gas and connect the vacuum source to the fluid sampling pump as described above.

FIG. 8 diagrammatically and schematically illustrates an exemplary leachate recovery, collection, and control system 210, according to the present invention, for withdrawing and collecting a flowable hazardous leachate material from a landsite 212, which has been divided into a number of cleanup cells 214. Each of the cleanup cells 214 includes a leachate recovery subsystem 216, including one or more preferred fluid-operated pump 220, each with an associated fluid control apparatus 222. As noted above, the invention is not limited to the leachate removal application shown in the drawings and discussed herein for purposes of illustration.

Each of the subsystems 216 includes leachate discharge piping 224 for conveying withdrawn leachate from the pumps 220 to a flow totalization unit 226. In turn, the recovery, collection and control system 210 includes leachate collection piping 228 for conveying leachate material from the flow totalization units 226 to a central collection tank or other receptacle 230. In this regard, it should be noted that the collection tank 230 can alternately be replaced by a railway tank car, a tank truck, or other stationary or portable collection receptacles, depending on the design parameters and site accessibility at a particular contaminated landsite. It should also be noted that in a given application, the contaminated landsite can be required to be divided into a greater or lesser number of cells than that illustrated schematically in FIG. 8, or in smaller scale operations, only a single subsystem 216 may be required to serve the recovery and collection needs at that landsite.

Figure 9:
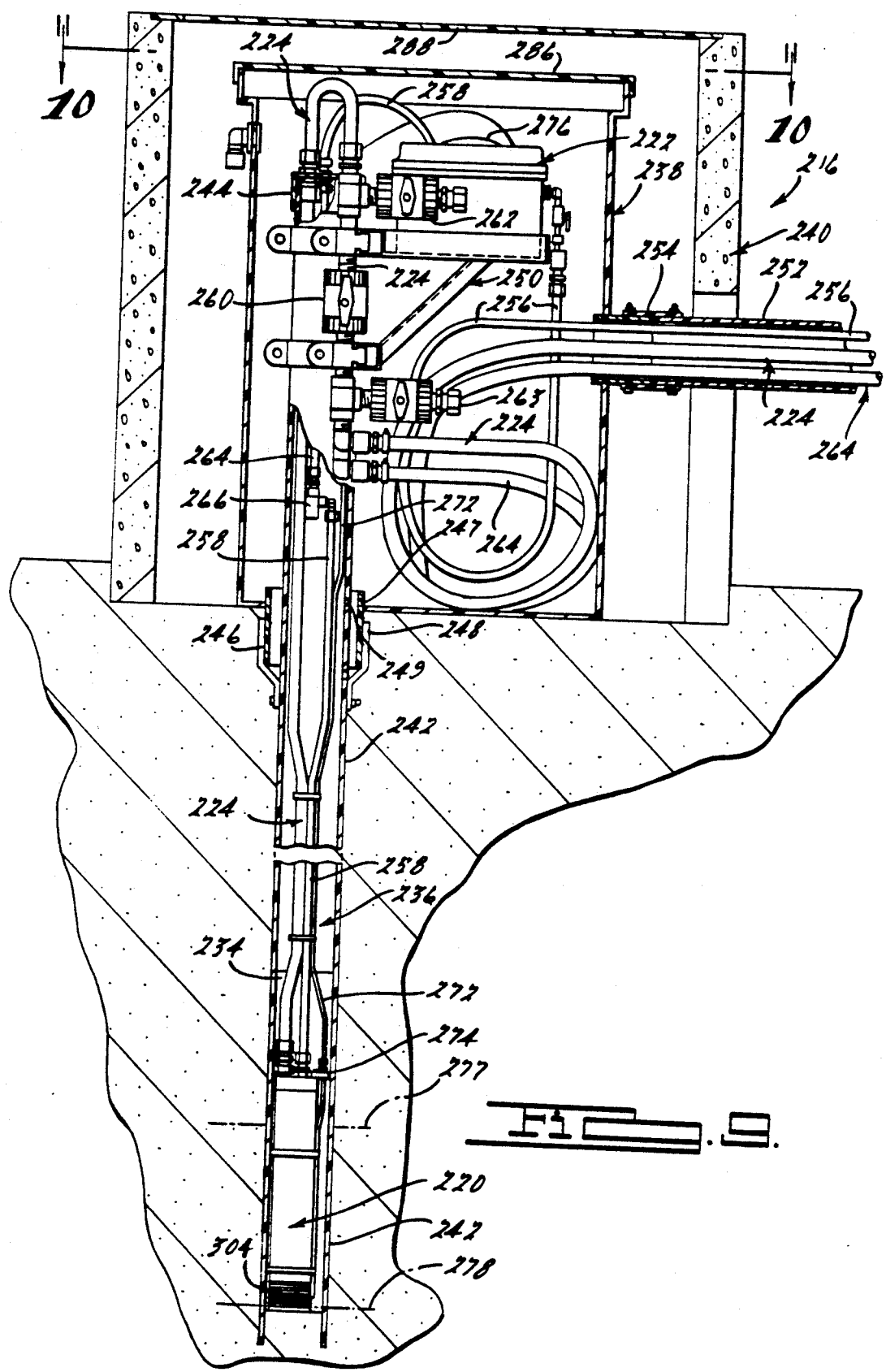
FIG. 9 is an elevational view, partially in cross-section, of a preferred fluid-operated recovery pump and fluid control apparatus for installation in an in-ground well at a landsite diagrammatically represented in FIG. 8.
Figure 10:
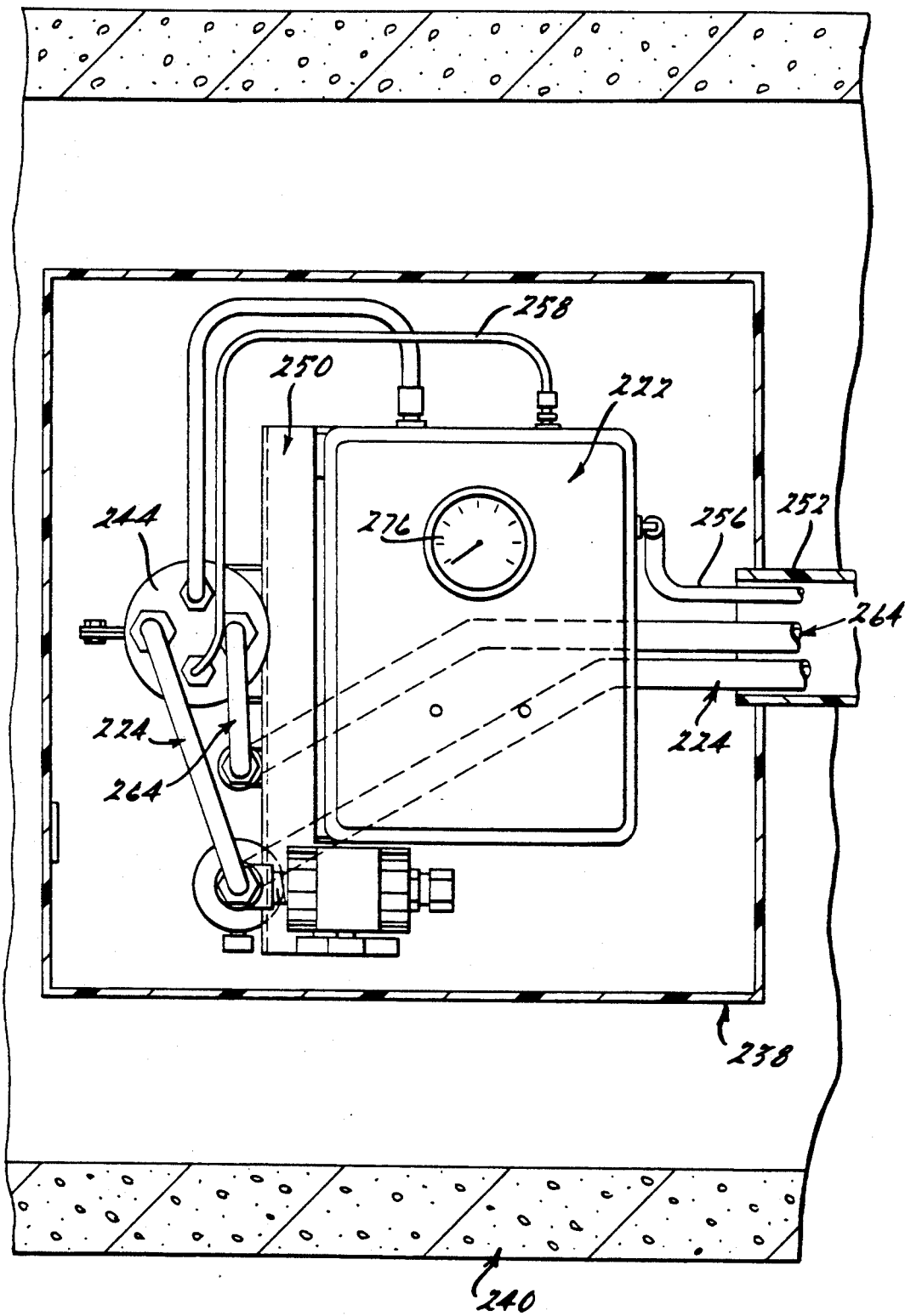
FIG. 10 is a view taken generally along line 10—10 of FIG. 9.
Figure 11:
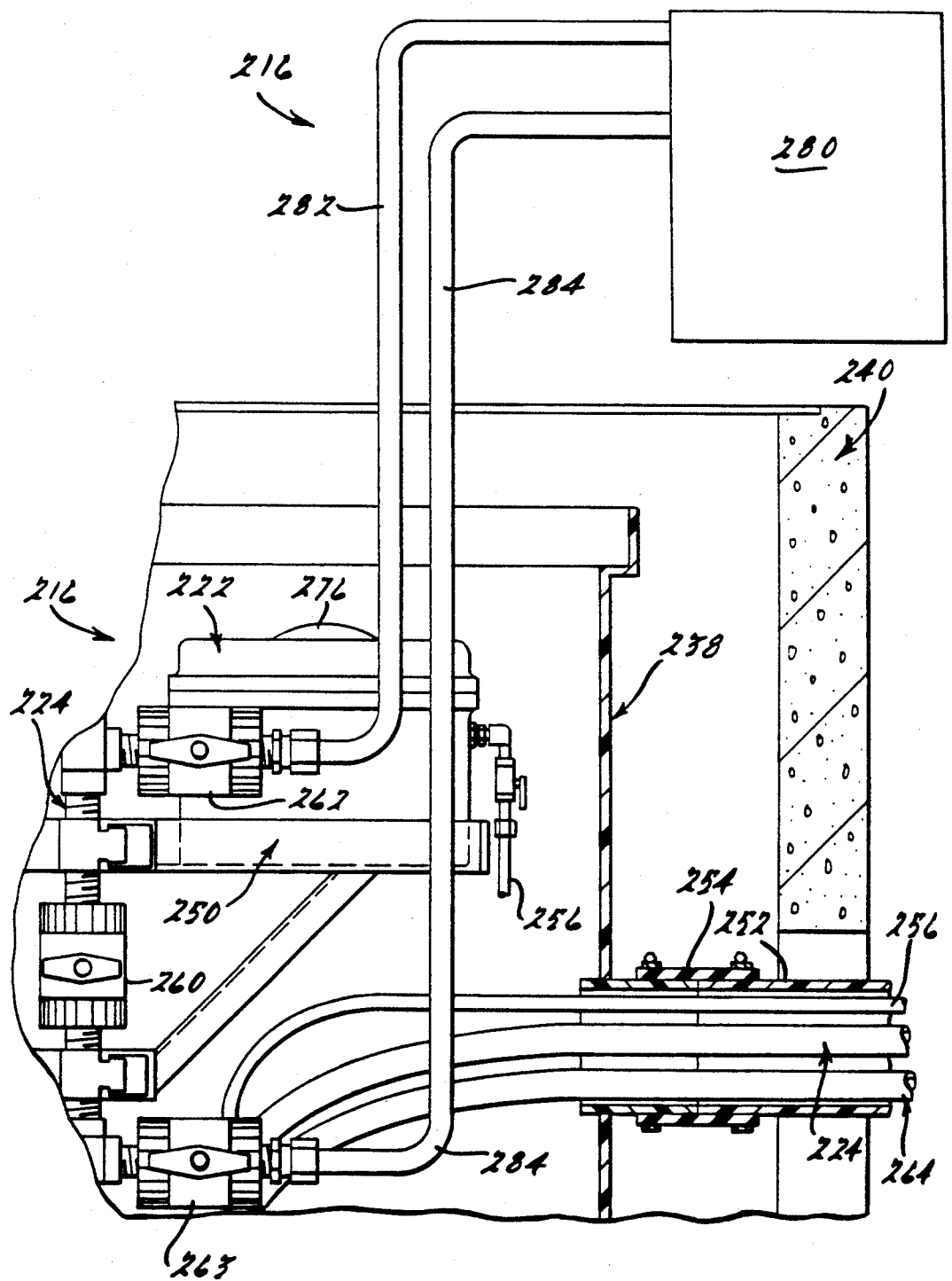
FIG. 11 is a partial, detailed view of a portion of FIG. 9, illustrating an optional portable flow measurement device interconnected with the recovery pump discharge.

As shown in FIGS. 9 through 11, each of the subsystems 216 preferably includes one or more of the pumps 220 submersed in in-ground wells 236 with the pumps 220 and associated fluid control apparatuses 222 housed within optional secondary containment structures 238, which are in turn surrounded by primary containment or protection structures 240. Each in-ground well 236 is equipped with a well riser or casing 242, which is closed off by a cap assembly 240 and interconnected with the secondary containment structure 238 by way of a wellhead boot 246 and a flexible coupling 254. Preferably, the wellhead boot 246 and the well casing 242 include one or more drain holes 247 and 249, respectively, for draining any leachate spills or leakage within the secondary containment 238 back into the well 236.

The pump and control apparatuses of each subsystem 216 are preferably separate components or component assemblies that are interconnected as a unitized assembly by way of bracket structures 250 attached to the well risers or casings 242. Such an arrangement provides for ease and convenience of installation or removal of each pump 220 and the fluid control apparatus 222, as a unitized assembly, while still allowing for ease and convenience of removal of separate components or assemblies. A secondary containment piping system 252 is also interconnected and preferably sealed with the secondary containment structure 238, which together provide optional secondary containment for any spills or leaks of hazardous leachate material in the piping in cleanup applications where such secondary containment is required or desirable.

The subsystem 216 also includes control fluid piping 256 interconnecting a source of pressurized air or other fluid (see FIG. 16) with each fluid control apparatus 222, and control fluid piping 258 is provided between each fluid control apparatus 222 and the associated fluid-operated pump 220, in order to allow the pumps 220 to be actuated, deactuated, and controlled by way of the fluid control apparatuses 222 in a manner described in more detail below.

Preferably, each in-ground well 236 of the subsystem 216 includes a static head or measuring fluid conduit 272, which is generally similar to the fluid conduit 54 described above in connection with FIGS. 1 through 7, and which has an open end extending beneath the surface of the leachate 234 in the in-ground well 236. An opposite end of the fluid conduit 272 is interconnected with the fluid control apparatus 222, which supplies air or other control fluid (as a measuring fluid) to the conduit 272 at a pressure sufficient to force some measuring fluid to bubble out of the open end of the conduit 272 against the static head of the leachate or other liquid. The pressure necessary to expel the leachate 234 from the open end of the static head conduit 272, and thus cause measuring fluid to bubble from the open end of the static head conduit 272, is directly indicative of the static head, and thus the standing level, of the leachate 234 in the in-ground well 236 can be sensed and monitored.

In a manner described in more detail below, the fluid control apparatus 222 and the fluid conduit 272 function to actuate and deactuate the pump 220 in response to respective predetermined high and low leachate levels in the in-ground well 236. The exact levels of such predetermined high and low leachate levels depend, of course, on the particular conditions at a given landsite application. However, for purposes of illustration, the predetermined high and low leachate levels are schematically indicated by reference numerals 277 and 278, respectively, in FIG. 9. In addition, the fluid conduit 272 is preferably interconnected with the body of the pump 220, or with the well casing 242, by way of an adjustment bracket 274 for purposes of easily adjusting the level at which the open end of the fluid conduit 272 is positioned within the in-ground well 236. Optionally, the fluid control apparatus 222 can be equipped with a gauge 276, as perhaps best shown in FIG. 10, for purposes of providing visual indication of the static head, and thus the level, of the leachate 234 in the in-ground well 236.

As shown in FIG. 9, the subsystem 216 can also optionally be provided with a vacuum system vacuum piping 264 extending through the primary containment structure 240, the secondary containment structure 238, and the well cap assembly 244, into an upper region of the well casing 242, where it terminates with a vacuum inlet 266. Such a vacuum system can optionally be provided in applications where hazardous gases are present or given off by the leachate. The optional vacuum piping 264 and vacuum inlet 266 can be interconnected in fluid communication with an air scrubber or other air cleaning equipment (not shown) for purposes of safely and properly removing and disposing of dangerous gaseous contaminants from the in-ground well 236 and the area of the contaminated landsite 212.

In addition to the above, the subsystem 216 includes a number of valves and fittings, including a discharge shut-off valve 260 provided in the leachate discharge piping 224, as well as a leachate discharge shut-off valve and quick-connect fitting assembly 262 and a similar leachate return shut-off valve and quick-connect fitting assembly 263, both of which are removably connectable to an optional portable flow measurement unit 280 shown in FIG. 11 and described below.

As shown in FIGS. 9 and 11, the secondary containment structure 238 and the primary containment structure 240 are equipped with covers 286 and 288, respectively, that can be removed to allow the optional portable flow measurement unit 280 to be interconnected with the fluid-operated pump 220 for purposes of testing or adjusting the leachate recovery subsystem 216. The optional portable flow measurement unit 280 is interconnected with the pump 220 and the leachate discharge piping 224 by way of discharge measurement piping 282, which is removably connectable to the quick-connect assembly 262 and the quick-connect assembly 263, respectively.

Referring to FIGS. 12 and 13, the preferred fluid-operated pump 220 is an air-operated gas-displacement pump, including a generally hollow cylindrical pump body 296 having an inlet cap 298 and an outlet cap 300 preferably threadably attached to its opposite ends. The inlet and outlet caps 298 and 300, respectively, are sealed with the pump body 296 by way of elastomeric O-rings 302 or other suitable sealing means known to those skilled in the art. The inlet cap 298 includes an inlet filter screen 304, having a number of openings 306 therein, for filtering out solids greater than a predetermined size, and a movable check valve ball 307 adapted for sealing engagement with a ball seat 308, in order to provide substantially one-way fluid flow from the in-ground well into the interior of the pump body 296. Similarly, the outlet cap 300 includes an outlet port 310 and a movable check valve ball 312 sealingly engageable with a ball seat 314 for providing substantially one-way fluid flow for discharging the leachate or other fluid from the pump 220. The outlet port 310 is preferably threadly connectable with the leachate discharge piping 224 (shown in FIG. 9).

A discharge tube 320 is provided within the interior of the pump body 296, preferably in a spaced relationship therewith, and has an open inlet end 322 in fluid communication with the interior of the pump body 296. Preferably, the open inlet end 322 includes a number of spaced discontinuities 324, with openings therebetween, in order to allow fluid flow from the interior of the pump body 296 into the discharge tube 320 even if the inlet check valve ball 307 contacts the open inlet end 322 of the discharge tube 320 during discharge fluid flow.

The outlet cap 300 also includes a gas supply inlet port 328 that is preferably threadably connectable with the control fluid piping 258 (shown in FIG. 9) for supplying air or other control fluid into the interior of the pump body 296. As will be explained in more detail below, the fluid control apparatus 222 (shown in FIGS. 8 through 11) sequentially and pulsatingly supplies pressurized air or other control fluid into the interior of the pump body 296 in order to forcibly displace and discharge leachate or other fluids through the discharge tube 320 and the outlet port 310 into the leachate discharge piping. Between pressure pulses, the pressure of the air or other control fluid in the interior of the pump body 296 is relieved or depressurized in order to permit the leachate 234 to flow, under the influence of its own static head, through the openings 306 of the inlet screen 304 and into the interior of the pump body 296. Thus because of the provision of the inlet check valve, leachate material within the interior of the pump body 296 is forced outwardly through the discharge tube 320 and the outlet port 310 during control fluid pressure pulses. Similarly, because of the provision of the outlet check valve ball 312 and the outlet ball seat 314, leachate material in the leachate discharge piping 224 is prevented from flowing in a reverse direction back into the interior of the pump body 296 during the relieving or depressurizing of the control fluid in the pump body 296 between control fluid pressure pulses.

It should be noted that in the preferred embodiment of the present invention, including the fluid measuring conduit 272 shown in FIG. 9 for sensing the level of the leachate material 234 in the in-ground well 236, the sequentially and pulsatingly alternating pressurizing and depressurizing of the air or other control fluid from the fluid control apparatus 222 does not occur until the leachate material 234 in the in-ground well 236 reaches the predetermined high level 227. Conversely, such sequential and pulsating pressurization of the control fluid by the fluid control apparatus 222 ceases when the leachate level in the in-ground well 236 reaches the predetermined low level 278. As a result of such operation of the fluid control apparatus 222, the pump 220 is actuated at the predetermined high leachate level 277 and deactuated at the predetermined low leachate level 278. The details of the operation of the preferred fluid control apparatus 222 to accomplish the above functions will be described in more detail below.

It should be noted that all the components of the pump 220 (as well as the other pumps shown in the various figures) are preferably composed substantially entirely of non-corroding materials that are resistant to any corrosive and destructive nature of the particular leachate being recovered. Although the exact materials will depend upon the particular leachate being recovered and are thus readily determinable by one skilled in the art, examples of synthetic materials that are resistant to many common leachate materials include polyethylene, polypropylene, or virgin grade tetrafluoroethylene. It should also be noted that such exemplary synthetic materials, or other suitable materials dictated by the composition of the particular leachate being recovered, should also be used wherever possible for the composition of the piping systems and all other components of the recovery, collection, and control system 210 disclosed and illustrated herein, at least in any instances where such components will routinely, or even potentially, come into contact with the leachate or other material being recovered and collected.

It should be noted from the description herein that the preferred subsystem 216 allows for easy and convenient removal of leachate or other liquid material from small-diameter wells, generally in the range of approximately two inches to approximately ten inches in diameter.

Referring to FIGS. 14 and 15, another embodiment of the flow totalization unit 226 includes a totalizer vessel 338, the interior of which is divided into an upper chamber 340 and a lower chamber 342 by a barrier 344 having openings 346 providing fluid communication between the upper chamber 340 and lower chamber 342. The totalizer vessel 338 also includes an inlet 348 adapted for connection in fluid communication with the leachate discharge piping 224, as shown in FIG. 8. The totalizer vessel 338 also includes a discharge outlet 350 adapted for connection and fluid communication with the leachate collection piping 228 between the flow totalization unit 226 and the central collection tank or other collection receptacle 230, as shown in FIG. 8. The totalizer vessel 338 is preferably integrally molded from a suitable non-corroding synthetic material, as discussed above, and includes a removable cover 352 thereon.

Discharge syphon piping 354 is provided within the interior of the totalizer vessel 338 and includes a first discharge leg 356 and a second discharge leg 357 interconnected in a generally U-shaped configuration. As shown in FIG. 14, the first discharge leg 356 extends upwardly through the barrier 344, with an open end disposed at a predetermined height above the barrier 344 within the upper chamber 340. Similarly, the second discharge leg 357 extends upwardly from the lower chamber 342 into the upper chambers 340, with an open overflow end disposed at a higher position within the upper chamber 340.

A generally hollow syphon dome 358 is provided on the barrier 344 in an overlying relationship with the open end of the first discharge leg 356. The interior 362 of the syphon dome 358 is in fluid communication with the lower chamber 342 by way of a relatively large dome opening 364 extending through the barrier 344. The dome interior 362 is also in fluid communication with the upper chamber 340 by way of a plurality of openings 360 provided at a low position in the sidewall of the syphon dome 358.

The flow totalization unit 226 is preferably adapted for a cyclable, self-actuating and self-deactuating, discharge operation, in which the totalizer vessel 338 receives recovered leachate material from the pumps 220, without discharging, until the leachate level in the totalizer vessel 338 reaches a predetermined high level indicated by reference number 366 in FIG. 14. The flow totalization unit 226 then discharges through the discharge outlet 350 until the leachate in the totalizer vessel 338 recedes to a predetermined low level, generally in the neighborhood of the level of the barrier 344. Once the leachate level in the totalizer vessel 338 has fallen to the predetermined low level, the discharge cycle terminates and the totalizer vessel 338 then receives leachate material from the pumps 220 until it again reaches the predetermined high level 366, with the volume of the leachate material between such high and low totalizer vessel levels consisting of a predetermined leachate discharge volume for each actuation/deactuation cycle of the flow totalization unit 226.

The above-described self-actuating and self-deactuating, cyclable discharge feature of the totalizer vessel 338 is preferably accomplished by way of the syphon dome 358, which is of a type sometimes referred to as a "dosing syphon". However, it should be noted that other cyclable discharge means can alternately be employed in given applications. The preferred syphon dome 358, with its associated discharge syphon piping 354 functions in the manner described below.

At the end of each discharge of the totalizer vessel 338, leachate material is present at generally equal levels, such as those indicated at reference numerals 367 and 368, in discharge legs 356 and 357, respectively. Thus, at the end of each discharge, the upper chamber 340, the syphon dome interior 362, and the upper portions of the discharge legs 356 and 357, all contain air generally at atmospheric pressure. As leachate material enters the totalizer vessel 338, through the inlet 348, the air in the syphon dome interior 362 is pressurized by the leachate material flowing through the openings 360 and rising in the syphon dome 358. At this point the leachate level in the syphon dome interior 362 rises, but more slowly than the leachate level in the upper chamber 340. Thus the air in the syphon dome interior 362 is pressurized by the rising leachate material in the syphon dome interior 362 and is forced downwardly in the discharge leg 356 as the syphon dome 358 and the upper chamber 340 continue to fill with leachate material. Ultimately, some of the air in the first discharge leg 356 begins to bubble into the second discharge leg 357, where the air bubbles rise and are released into the upper region of the upper chamber 340, thus allowing leachate in the syphon dome interior 362 to reach the open top end of the first discharge leg 356. A syphon effect is thus established in the discharge syphon piping 354, generally at a point coincident with the leachate material reaching the high level 366 in the upper chamber 340, and substantially all of the leachate material in the upper chamber 340 flows through the discharge piping 350 in a continuous syphon discharge flow.

The above-discussed continuous syphon discharge flow from the totalizer vessel 338 continues until the leachate material recedes to a level generally at or adjacent the barrier 344, at which time the syphon effect is destroyed by the entry of sufficient air into the syphon dome interior 362, and the discharge flow ceases. The leachate levels in the discharge legs 356 and 357 again return to equilibrium, with the discharge syphon piping functioning generally as a trap, and the filling portion of the cycle described above starts again. By such an arrangement, substantially no leachate material flows out of the totalizer vessel 338 between discharges, and thus the amount of leachate discharged over a preselected time period can be accurately determined. As indicated above, and discussed in more detail below, the totalizer vessel 338 is preferably adapted to be calibrated so that a known, predetermined volume of leachate material is discharged during each actuation/deactuation cycle.

Preferably, the flow totalization unit 226 also includes a device or apparatus for counting and recording the number of discharge cycles of the totalizer vessel 338 over a preselected time period in order to allow for the accounting of the amount of hazardous leachate material recovered and collected by the leachate recovery and collection system 210 in FIG. 8. In one exemplary embodiment of the preferred flow totalization unit 226, such counting and summing feature is provided by way of a mechanical float-type counter 370 illustrated in FIG. 14, which includes a float 372 attached to a pivot arm 374 for actuating a counting apparatus 375 each time the level of the leachate material in the totalizer vessel 338 rises and falls during a complete actuation/deactuation discharge cycle. Such counting apparatus 375 can alternately consist of any of a number of counting and summing devices known to those skilled in the art, such as electric or electronic counters, photoelectric counters, or the like, but should not consist of an electrical device in applications wherein hazardous explosive gases are present.

In order to aid in the installation and set-up of the flow totalization unit 226, the exemplary totalizer vessel 338 in FIG. 14 is equipped with a plurality of calibration dishes 376, which are preferably integrally-molded with the barrier 344 and have open upper ends in communication with the upper chamber 340. Such calibration dishes 376 allow the flow totalization unit 226 to be calibrated for a preselected, predetermined volume of leachate discharge during each discharge cycle. Such a calibration is accomplished by measuring the volume of fluid discharged during a test actuation/deactuation cycle. If the test discharge volume is required to be increased in order to obtain the preselected, predetermined discharge volume, such adjustments can be incrementally made by merely drilling or otherwise forming an opening through the barrier 344 within one or more of the calibration dishes 376, such as the calibration opening 378 illustrated in phantom lines in FIG. 15. By providing such fluid communication between the interior of one or more of the calibration dishes 376 and the lower chamber 342, by way of the calibration openings 378, the leachate material within each of the opened-up calibration dishes 376 is allowed to be discharged during each gravity or syphon flow discharge cycle, while the leachate material in any of the calibration dishes 376 that have not been provided with openings 378 will remain within the closed calibration dishes 376, as the leachate level falls during discharge, and will not be discharged.

The fluid control system for the fluid control apparatus 222 is preferably all pneumatic and functions in a manner quite similar to that of the fluid controller apparatus 50 described above and illustrated schematically in FIGS. 3 and 3A. As represented schematically in FIG. 16, a pressurized actuating gas, such as air, for example, is supplied from an actuating gas source 424, such as a gas compressor or pressurized gas containers located in a suitable location at or near the contaminated landsite. The control fluid or actuating gas is supplied to the fluid control apparatus 222 by way of a supply line 426, and is further controlled and conveyed to the preferred fluid-operated pumps 220 by way of supply lines 426A, 426B, and 426C, which are connected in fluid communication with the air or other fluid control piping 258 shown in FIG. 9. It should be noted that the control logic described below can be disposed in the pump assembly, in the in-ground well, or in the control apparatus 222.

The alternately pulsating pressurization and depressurization of the control fluid during actuation of the pump 220 is controlled by the action of a supply valve 428, which is in fluid communication with the actuating and control fluid source 424 and the supply lines 426, 426A, 426B, and 426C. In its first valving mode, which is shown in FIG. 16, the supply valve 428 connects the preferred compressed air actuating and control fluid source 424 to the fluid control piping 258 and the pump 220 in order to pressurize the interior of the pump body 296, thereby forcibly displacing the leachate material from the pump 220 (as described above).

The supply valve 428 is urged into its first valving mode (shown in FIG. 16) by operation of the leachate level sensing system for monitoring the leachate level in the well 236, as described above. Such leachate level sensing system is supplied by control fluid from the actuating and control fluid source 424 by way of conduits 426, 426A, and a conduit 402, which provides fluid communication with the fluid measuring conduit 272 by way of an optional regulator 403 and a flow restrictor 404. When the back pressure in the fluid measuring conduit 272 increases to a level sufficient to indicate a leachate level corresponding to the predetermined high level 277 shown in FIG. 9, the pressurized control fluid in the fluid measuring conduit 272 is conveyed through a conduit 411 to an amplifier valve actuator 412 for an amplifier valve 410 at a pressure sufficient to cause actuation of the pump 220.

Figure 16:
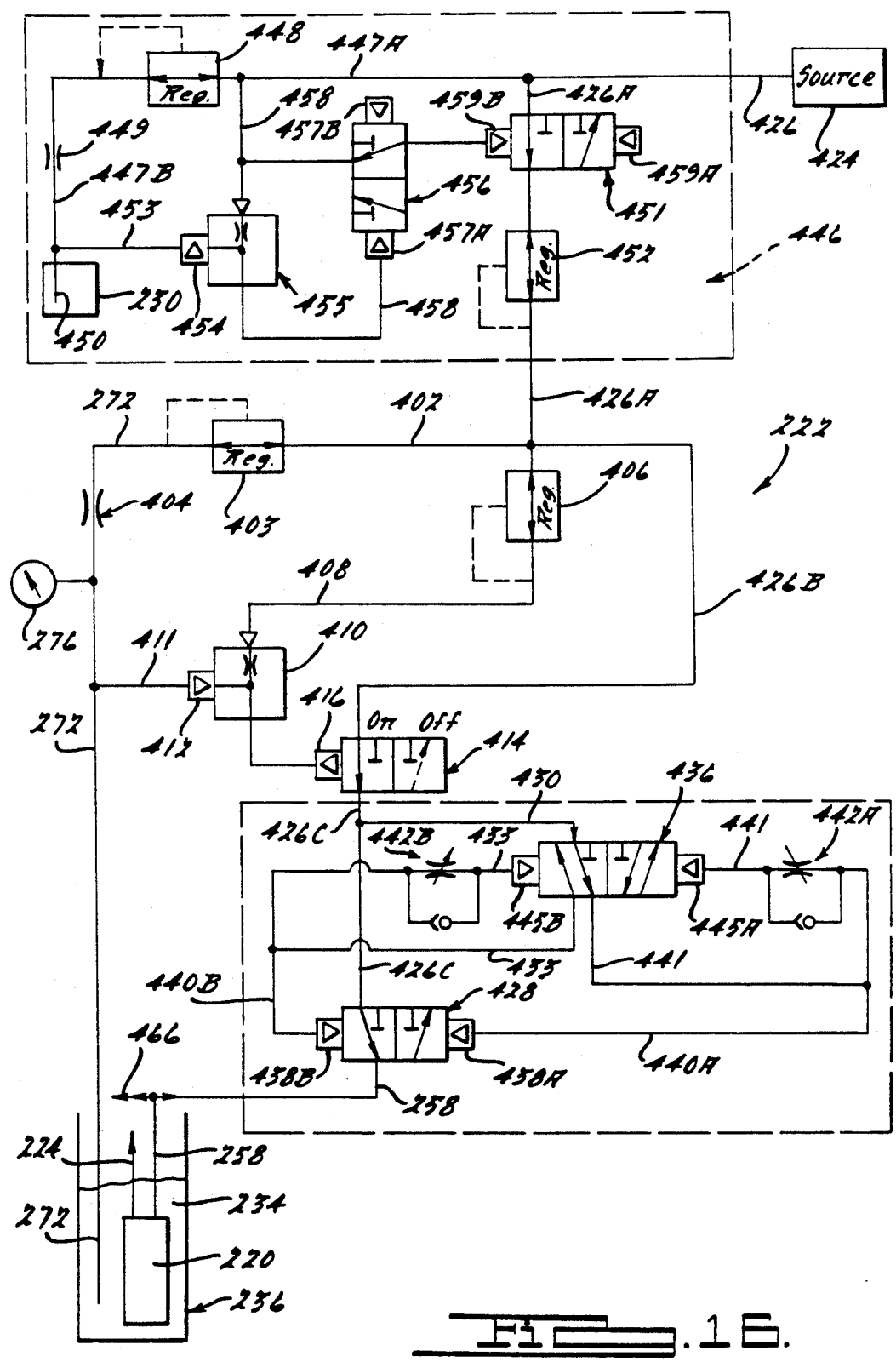
FIG. 16 is a schematic diagram of an operating fluid control system for the recovery and collection system.

When the pressure signal from the amplifier valve 410 is sufficient to overcome the normally-off condition of an on/off valve actuator 416 for an on/off valve 414, shown in FIG. 16, the pressurized control fluid in conduit 426B is permitted to flow through the on/off valve 414 into the conduit 426C to the supply valve 428, thereby allowing actuation of the fluid-operated pump 220. Such on-off actuator 416 can be independently adjustable, or can have a fixed actuation point, depending upon the particular control application. Conversely, when the leachate material 234 in the well 236 falls to the predetermined low leachate level 278 shown in FIG. 9, the back pressure in the fluid measuring conduit 272 is at a correspondingly reduced level indicative of the reduced static head of the leachate material 234, thus rendering the amplifier valve 410 incapable of overcoming the normally-off condition of the on/off valve actuator 416, which in turn consequently urges the on/off valve 414 to its off position and preventing supply of pressurized actuating and control fluid to the fluid-operated pump 220 in order to deactivate the pump.

Pressurized control fluid from the fluid source 424 is also conveyed through the conduits 426, 426A and 426B, through the on/off valve 414 (when open), and into a conduit 430 to a control shuttle valve 436, which directs the pressurized control fluid to one of the two pilot actuators 438A and 438B of the supply valve 428. When control shuttle valve 436 is in its first valving mode shown in FIG. 16 a conduit 441 is pressurized, the pilot actuator 438A on the supply valve 438 is pressure-actuated through a conduit 440A, and the pilot actuator 445B is vented to atmosphere. As the fluid pressure in the conduit 441, which supplies the fluid actuator 445A for the control shuttle valve 436, exceeds a predetermined level, the control shuttle valve 436 is urged into a second valving mode. In such second mode, the control fluid in the conduit 430 flows through the control shuttle valve 436 into a conduit 433 and a conduit 440 B in order to cause the actuator 438B on the three-supply valve 428 to cause the supply valve 428 to be pressure-actuated into a second valving mode wherein the pressure in the fluid control piping 258 is vented to atmosphere, thereby relieving the actuating fluid pressure in the interior of the fluid-operated pump 220. When the pressure in the conduit 433 builds to a sufficient level, the actuator 445B on the control shuttle valve 436 causes the control shuttle valve 436 to be pressure-actuated back to the first valving mode shown in FIG. 16, thereby again pressurizing the actuating fluid in the fluid-operated pump 220.

Such sequentially alternating reversals of the valving mode positions of the control shuttle valve 436 and the fluid control valve 428 occur in rapid succession, the timing of which can preselectively altered or adjusted by way of the flow control valves 442A and 442B, which are in fluid communication with the actuators 445A and 445B, respectively. Thus, the conduits 440A and 440B are alternately, sequentially and pulsatingly pressurized and depressurized for time periods that are controlled by the control fluid pressures flowing through the flow control valves 442A and 422B. As a result, the sequentially, alternating and pulsating pressurization and depressurization of the interior of the pump 220, during its actuation condition cause a gas-displacement, pulsating discharge of the leachate material 234 in the well 236 to the leachate discharge piping 224. Such pulsating operation cannot, of course, occur if the on/off valve 414 is in its "off" condition, wherein it prevents flow of pressurized control and actuating fluid from the conduit 426B into the conduit 426C.

The fluid control apparatus 222, which is preferably all pneumatic, can also optionally include a level sensing and control system 446 for sensing and monitoring the level of collected leachate material in the collection tank or other receptable 230 shown in FIG. 8. As illustrated in FIG. 16, a level sensing and control system 446 for the collection tank 230 includes an on/off valve 451, which is preferably fluid-actuated in a manner similar to the on/off valve 414 described above, with the exception that the on/off valve 451 is in its "on" valving mode when the leachate level in the collection tank 230 is below a maximum "shut-off" level. Because of this difference, a signal processing valve 456 is required in order to effectively reverse the "direction" or "sense" of operation of the on/off valve 451 with respect to that of the operation of the on/off valve 414.

In the level sensing and control fluid system 446, fluid from the actuating and control fluid source 424 is conveyed through the conduit 426, and into the conduit 447A, and optional regulator 448, a flow restrictor 449, and a conduit 447B, into a fluid measuring conduit 450 in the collection tank 230. The fluid measuring conduit 450 is substantially identical in function to that of the fluid measuring conduit 272 described above, and is similarly easily adjustable at preselected levels in the collection tank 230. Control or measuring fluid is supplied to the fluid measuring conduit 450 at a pressure sufficient to force the measuring fluid to bubble out of an open end of the conduit 450, with the back pressure of such fluid being indicative of the static head (and thus the level) of the leachate material in the collection tank 230. When the back pressure of the control fluid in the conduit 447B is sufficient to indicate a preselected maximum or "shut-off" level of leachate material in the collection tank 230, such pressurized control fluid is conveyed by way of the conduit 453 to an amplifier valve actuator 454 for an amplifier valve 455 at a pressure sufficient to cause a shut off of the supply of actuating fluid to the pump 220. The amplifier valve 455 accomplishes this by increasing the pressure of the control fluid in a conduit 458 (connected to the above-mentioned conduit 447A through the amplifier valve 455) to a level sufficient to cause a pilot actuator 457A on the signal processing valve 456 to pressure-actuate the signal processing valve 456 out of the valving mode shown in FIG. 16. In this condition, pressurized control fluid in the conduit 447A cannot flow through the signal processing valve 456 into the pilot actuator 459B of the on/off valve 451. In such a case, the "normally off" actuator 459A will cause the on/off valve 451 to be pressure-actuated away from its "on" valving mode shown in FIG. 16 and thereby prevent flow of control and actuating fluid from the conduit 426 into the conduit 426A and through the remainder of the fluid control apparatus 422 to the pump 220.

Conversely, when the level of the leachate material in the collection tank 230 is below the preselected maximum "shut-off" level, the amplifier valve 455 will permit the signal processing valve 456 to assume the "on" valving mode shown in FIG. 16, which in turn allows flow of control fluid to the actuator 459B of the on/off valve 451. In such a condition, the on/off valve 451 is maintained in its "on" valving mode, as shown in FIG. 16, and the fluid control apparatus 222 and the pumps 220 are permitted to remain in an "on", or available, condition for leachate recovery and collection as described above.

It should be noted that alternate apparatuses, such as electrical or electronic systems, can be used for automatically cycling the pumps 220 and/or the supply valve 428 between pressurization and depressurization modes, in lieu of the preferred all pneumatic system. For example, electronic timers can be used to control alternate solenoid-operated versions of the supply valve 428, with one timer controlling the duration of each position or valving mode of the supply valve 428. Such electric or electronic apparatuses can, of course, only be used in leachate recovery, collection, and control systems used in cleanup operations where no hazardous explosive gases are present. Similarly, alternate pneumatic or other fluid control circuits can also be provided for the supply valve 428, in a manner similar to that discussed above and represented schematically in connection with FIG. 3A for the fluid controller 50, with other alternate timing elements. One skilled in the art of pneumatic and other control systems (such as electric or electronic systems) will readily recognize that the selection among the various control systems discussed herein is based upon considerations of reliability, ease of operation, economy, flexibility, and the particular parameters of a given application for which use of the present invention is contemplated.

An optional exhaust or relief valve, indicated by reference numeral 466 in FIG. 16, can be provided if deemed necessary or desirable to facilitate the quick-operating depressurization of the pump 220 in a given application. Also, the exhaust valve 466 can advantageously be located close to the associated pump to be used for discharging entrained liquids back into the well or containment structure from the control system, to exhaust vapors back into the well or containment, and to enhance exhaust efficiency.

FIG. 17 illustrates a representative example of a secondary piping containment feature, which can optionally be employed in conjunction with the present invention. In FIG. 17, the secondary containment piping 252 (also shown in FIGS. 9 through 11) is interconnected with a secondary containment junction box 460, by way of a flexible coupling 254, for housing various valving and interconnection of representative piping junction 462. Such a representative piping junction 462 can consist of actuating and control fluid piping, leachate piping, exhaust piping, or any of the other piping systems employed in connection with the present invention. Such secondary containment feature can optionally be provided wherever required or desirable in order to provide physical protection for the piping or other conveying systems of the present invention, as well as where secondary containment of possible leachate spills or leaks is desired or necessary. Preferably, the secondary junction box 460, like the secondary containment piping 252 and virtually all other equipment in the system 210, is molded from a synthetic, non-corroding material, such as one of the materials discussed above in connection with the composition of the components for the pumps 220.

FIGS. 18 through 24 illustrate a pump 520, including an improvement according to the present invention. It should be noted that such improvement, although shown for purposes of illustration in the exemplary pump 520, is equally applicable to the fluid sampling pump 20, any of the other pumps depicted in the various drawing figures, and other types of pumps, including non-bladder pumps. It should further be noted that some of the components or features depicted in FIGS. 18 through 24 are similar, either in configuration or function, to various components or features shown and described in connection with FIGS. 1 through 17. Therefore, in FIGS. 18 through 24, such similar components or features are indicated by reference numerals similar to the corresponding components or features in the other drawing figures, but having either five-hundred, six-hundred, or seven-hundred prefixes in FIGS. 18 through 24.

Figure 18:
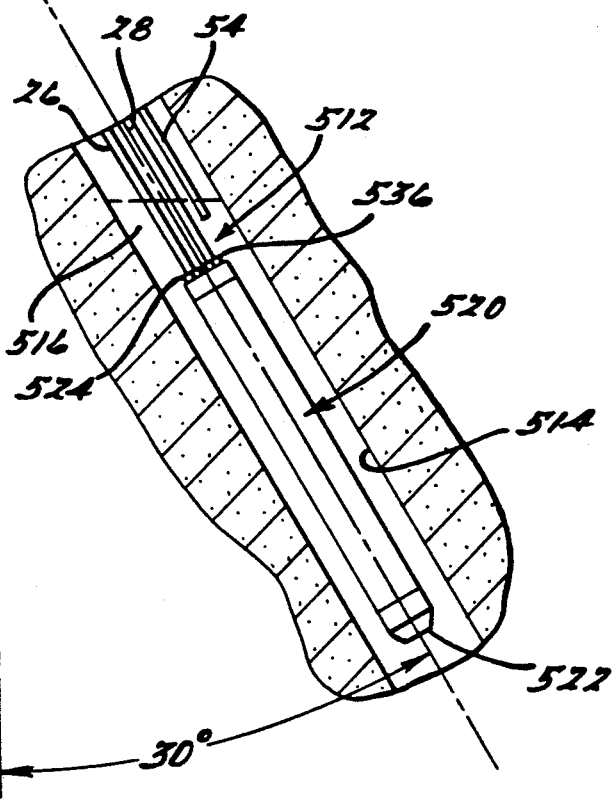
FIG. 18 is a partial view, somewhat similar to a portion of FIG. 1, but illustrating a pump capable of operation in vertical, non-vertical, or even inverted orientations according to the present invention.
Figure 18A:
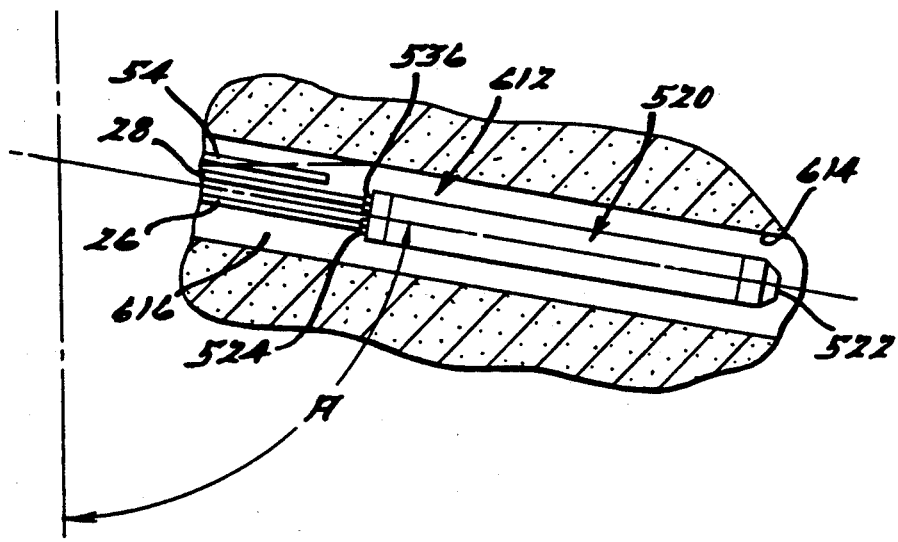
FIG. 18A is a view similar to that of FIG. 1, but illustrating the pump of FIG. 1 in another, nearly horizontal orientation.

In FIGS. 18 and 18A, the pump 520 is depicted as disposed within wells 512 and 612, respectively, with such wells 512 and 612 being oriented in non-vertical orientations. In FIG. 18, the well 512 extends in an orientation approximately 30 degrees from the vertical. At such approximate angled orientation, the previously-described pumps have been found to be incapable of functioning properly due to the provision in such previously-described pumps of a ball-and-seat check valve arrangement with a gravity-return ball. Thus, in orientations that are inclined approximately 30 degrees or more to the vertical, it is necessary to provide an alternate check valve arrangement. Such alternate check valve arrangement, which is described in more detail below, is capable of rendering the pump 520 functional in a vertical orientation, an inclined or angular orientation, a horizontal orientation, or even an inverted orientation. Thus the two illustrative orientations depicted in FIGS. 18 and 18A, wherein the respective wells 512 and 612 are disposed at non-vertical orientations, are meant to serve merely as examples of the orientations at which the pump 520 according to the present invention is fully functional.

In FIG. 19, the pump 520 is substantially similar to the exemplary fluid sampling pump 20 and the other pumps described above and shown in FIGS. 1 through 17, except for the provision of a reed-type check valve arrangement, with reed check valve 568 being provided for one-way flow adjacent the inlet 522, and with reed check valve 576 being provided for one-way flow at the outlet end of the pump 520. Except for differences in size for accommodating different sizes of flow openings at opposite ends of the pump 520, as shown for purposes of example of FIG. 19, the reed check valve 568 and the reed check valve 576 are substantially identical. Thus, in FIGS. 20 through 23, only the reed check valve 568 is illustrated as a typical construction.

As shown in FIGS. 19 through 23, the reed check valve 568 and the reed check valve 576 have a generally frusto-conical configuration and are composed of a resilient flexible material, such as rubber, neoprene, vinyl, or other resiliently deflectable materials suitable for the fluid being pumped or for its corrosive characteristics. An example of a reed check valve member that has been found to perform quite well in a variety of pumping applications is manufactured by Vernay Products, of Yellow Springs, Ohio. Such reed-type check valves have previously been used primarily in gas fluid conveying systems, but have been found to perform very advantageously in the application of the present invention.

The reed check valve 568 in FIGS. 20 through 23, which is substantially identical to the reed check valve 576, includes a body portion 563 having a flanged portion 576 at its inlet end, a tapered portion 567 at its opposite end, with an internal flow portion 569 extending therethrough. At the outlet end of the tapered portion 567, a flexible, resilient lip 571 is formed, with the lip 571 being resiliently biased by way of the construction and configuration of the reed check valve member 562 to a normally-closed position illustrated in FIG. 22. However, when a sufficient fluid pressure is present within the internal flow portion 569, such that the inherent resilient biasing of the lip 571 to its closed position can be overcome, the lip 571 resiliently deforms to form an exit flow opening 573, as illustrated in FIG. 23. Thus, when the reed check valve member 562 is in its closed position illustrated in FIG. 22, any back pressure at the outlet end does not result in a back-flow, such as that indicated by the back-flow arrow 575 in FIG. 22, and in fact tends to further urge the lip 571 toward its closed position in order to inhibit back-flow from the outlet end to the inlet end of the reed check valve member 562. In contrast, as mentioned above, the existence of a sufficient fluid pressure in the internal flow portion 569 results in the above-described resilient outward deformation of the lip 571 in order to allow normal one-way flow through the reed check valve member 562, as illustrated by flow arrow 577 in FIG. 23. As mentioned above, such a reed check valve can also be used in non-bladder type pumps, as well as the exemplary bladder-type pump shown in the drawings.

It should be noted that other check valve configurations or arrangements were tried in order to render the pump capable of functioning in non-vertical or inverted orientations, such as a ball-and-seat check valve arrangement similar to that described above and shown in FIG. 2, but having a spring-loaded return for resiliently urging the ball against its seat in order to seal the ball against back-flow pressure. However, such an arrangement was found to be unsatisfactory due to the relatively high level of pressure or static head necessary to overcome the return spring during normal one-way flow. As a result, pumps having such an arrangement were found to be lacking in performance in applications were insufficient static head was present in a well, tank, or other vessel in order to overcome the force of the return spring. Thus, the above-described reed-type check valve was tried and it was found, rather surprisingly, that such a check valve member, which is normally primarily used in gas flow applications, performed very satisfactorily in various applications for the pump 520.

Referring to FIG. 19, an additional feature is illustrated, which represents a modification over the basic design of the fluid sampling pump 20 shown in FIG. 2. Such additional feature is provided by way of an anti-chafe sleeve 579 disposed between the pump body 560 and the pump bladder 590, in a generally surrounding relationship with the pump bladder 590. The anti-chafe sleeve 579 is open to fluid flow at one or both of its ends and is provided for purposes of protecting the pump bladder 590 from wear or destruction resulting from excessive laterally-outward expansion or from abrasive chafing or rubbing contact with the interior of the pump body 560. Although not essential to the operation of the pump 520, the provision of the anti-chafe sleeve 579 has been found to significantly decrease the wear on the pump bladder 590, thus increasing the life of the bladder 590 and the pump 520 in many applications.

FIG. 24 illustrates an additional embodiment of the present invention, wherein the exemplary pump 520 is installed in a well drilled substantially horizontally, for example. In the embodiment of FIG. 24, the pump inlet 522 is attached in fluid communication with one end of a flexible hose 790 having its opposite, open inlet end 794 submerged in the liquid 716. This arrangement allows for pumping from such a horizontal, or near-horizontal, well to a very low liquid level. Such low level can be even further minimized by providing a hose inlet weight 792 at the hose inlet end 794 in order to enhance the downward deflection of the flexible hose 790. In either example, a reed check valve, such as that described above, can be provided either in the pump inlet 522 or in the hose inlet end 794, as well as in the pump outlet, if deemed necessary in a given application of the invention.

Although various examples of an application of the invention in a bladder-type pump have been shown and described for purposes of illustration herein, one skilled in the art will readily recognize that the invention is equally applicable to a wide variety of other types of pumps, including pumps not having a flexible bladder.

The foregoing discussion discloses and describes exemplary embodiments of the present invention. One skilled in the art will readily recognize from such discussion, and from the accompanying drawings, that various changes, modifications and variations may be made therein without departing from the spirit and scope of the invention as defined in the following claims.

What is claimed is:

1. A gas-actuated liquid pump adapted to be at least partially submerged within a liquid to be pumped, said liquid pump comprising: a pump body, a liquid inlet, a liquid outlet, a gas chamber in said pump body for receiving a gas therein, a liquid chamber in said pump body in fluid communication with said liquid to be pumped longitudinally through said inlet, a flexible bladder isolating said gas chamber form said liquid chamber, said flexible bladder being selectively deformable in response to changes in the pressure of said gas in order to cause said liquid to flow through said liquid chamber from said inlet to said outlet, inlet check valve means between said inlet and said liquid chamber for allowing one-way flow of said liquid therethrough from said inlet to said liquid camber and for substantially preventing back-flow of said liquid therethrough from said liquid chamber to said inlet regardless of the vertical, horizontal, non-vertical, or inverted orientation of said pump, outlet check valve means between said outlet and said liquid chamber for allowing one-way flow of said liquid therethrough from said liquid chamber to said outlet and for substantially preventing back-flow of said liquid therethrough from said outlet to said liquid chamber regardless of the vertical, horizontal, non-vertical, or inverted orientation of said pump, and anti-chafe means generally surrounding said flexible bladder and disposed between said flexible bladder and the interior of said pump body for substantially preventing contact of said flexible bladder with said pump body, each of said inlet and outlet check valve means including a reed-type check valve member having a body portion having an internal flow opening extending therethrough, a flange portion at one end of said body portion surrounding said internal flow opening in sealing engagement with said pump adjacent said inlet, and a lip portion at the opposite end of said body portion resiliently deflectable between an open position in communication with said internal flow opening for allowing said one-way flow therethrough and a closed position blocking off said internal flow opening for substantially preventing said back-flow therethrough, said lip portion being resiliently biased toward said closed position, said lip portion being resiliently deflectable to said open position in response to a predetermined liquid pressure within said internal flow opening, said lip portion being further biased toward said closed position by a back-pressure exerted thereon from within said liquid camber, said reed-type check valve member including a generally frusto-conical tapered portion converging toward said opposite end of said body portion and defining said lip portion at said opposite end, said anti-chafe means including an anti-chafe sleeve disposed between said flexible bladder and the interior of said pump body in a laterally generally-surrounding relationship with sad flexible bladder, said anti-chafe sleeve having at least one open unsecured end portion thereon providing fluid communication between the interior of said anti-chafe sleeve and said gas chamber.

2. A pump according to claim 1, further including a flexible hose in fluid communication with said liquid inlet, said flexible hose having an inlet end submersible in the liquid to be pumped, and further including a weight interconnected with said flexible hose generally at said inlet and in order to deflect said flexible hose generally downwardly.

* * * * *

UNITED STATES PATENT AND TRADEMARK OFFICE
CERTIFICATE OF CORRECTION

PATENT NO. : 5,147,185

DATED : Sep. 15, 1992

INVENTOR(S) : K. Lynn Niehaus; Kevin L. Newcomer; Steven C. Richter

It is certified that error appears in the above-identified patent and that said Letters Patent is hereby corrected as shown below:

Col. 1, Line 34, "ben" should be --been--;

Col. 1, Line 67, "collections" should be --collection--;

Col. 2, Line 44, "still" should be --steel--;

Col. 3, Line 20, "had" should be --head--;

Col. 4, Line 10, "providing" should be --provided--;

Col. 4, Line 12, "charged" should be --discharged--;

Col. 4, Line 59, "The" (1st occurrence) should be --the--;

Col. 6, Line 13, "red" should be --reed--;

Col. 6, Line 19, "illustration" should be --illustrating--;

Col. 6, Line 54, "produce" should be --product--;

Col. 6, Line 67, after "present" insert --invention--;

Col. 7, Line 7, "o" should be --of--;

Col. 7, Line 36, "potable" should be --portable--;

Col. 7, Line 53, "liquid" should be --fluid--;

Col. 8, Line 22, "pot" should be --port--;

Col. 9, Line 7, "drawing" should be --drawn--;

Col. 9, Lines 24-25, "teflon" should be --Teflon--;

Col. 10, Line 37, "this" should be --thus--;

Col. 10, Line 46, "as" should be --gas--;

Col. 10, Line 52, "as" should be --gas--;

Col. 10, Line 56, "times" should be --timers--;

Col. 10, Line 57, "time" should be --timer--;

Col. 10, Line 63, "142A" (2nd occurrence) should be --142B--;

Col. 11, Line 1, "each" should be --ease--;

UNITED STATES PATENT AND TRADEMARK OFFICE
CERTIFICATE OF CORRECTION

PATENT NO. : 5,147,185

DATED : Sep. 15, 1992

INVENTOR(S) : K. Lynn Niehaus; Kevin L. Newcomer; Steven C. Richter

It is certified that error appears in the above-identified patent and that said Letters Patent is hereby corrected as shown below:

Col. 11, Line 22, "closing" should be --closely--;

Col. 11, Line 41, "for" should be --from--;

Col. 12, Line 26, "as" should be --gas--;

Col. 13, Line 4, "pup" should be --pump--;

Col. 13, Line 10, "cases" should be --causes--;

Col. 14, Line 54, before "fluid" insert --control--;

Col. 16, Line 23, "threadly" should be --threadably--;

Col. 21, Line 39, after "can" insert --be--;

Col. 21, Line 46, "422B" should be --442B--;

Col. 23, Line 40, before "junction" insert --containment--;

Col. 24, Line 29, "of" should be --in--;

Col. 25, Line 23, "were" should be --where--;

Col. 26, Line 19, Claim 1, "form" should be --from--;

Col. 26, Line 27, Claim 1, "camber" should be --chamber--;

Col. 26, Lines 59-60, Claim 1, "camber" should be --chamber--;

Col. 26, Line 67, Claim 1, "sad" should be --said--.

Signed and Sealed this

Eighteenth Day of January, 1994

*Attest:*

BRUCE LEHMAN

*Attesting Officer*     *Commissioner of Patents and Trademarks*